US010591458B2

(12) United States Patent
Parker et al.

(10) Patent No.: US 10,591,458 B2
(45) Date of Patent: Mar. 17, 2020

(54) ANISOTROPIC MUSCULAR TISSUE DEVICES WITH INTEGRATED ELECTRICAL FORCE READOUTS

(71) Applicant: President and Fellows of Harvard College, Cambridge, MA (US)

(72) Inventors: Kevin Kit Parker, Cambridge, MA (US); Johan Ulrik Lind, Boston, MA (US); Jennifer Ann Lewis, Cambridge, MA (US); Joost Johan Vlassak, Lexington, MA (US); Hongyan Yuan, Cangzhou (CN); Travis Alexander Busbee, Somerville, MA (US); Ian Perkins, Bridgewater, MA (US); Christophe Chantre, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 255 days.

(21) Appl. No.: 15/116,258

(22) PCT Filed: Feb. 18, 2015

(86) PCT No.: PCT/US2015/016395
§ 371 (c)(1),
(2) Date: Aug. 3, 2016

(87) PCT Pub. No.: WO2015/178980
PCT Pub. Date: Nov. 26, 2015

(65) Prior Publication Data
US 2017/0016875 A1    Jan. 19, 2017

Related U.S. Application Data

(60) Provisional application No. 61/941,119, filed on Feb. 18, 2014.

(51) Int. Cl.
G01N 33/483    (2006.01)
A61B 5/00      (2006.01)
A61B 5/053     (2006.01)

(52) U.S. Cl.
CPC ......... *G01N 33/4833* (2013.01); *A61B 5/053* (2013.01); *A61B 5/4519* (2013.01)

(58) Field of Classification Search
None
See application file for complete search history.

(56) References Cited

U.S. PATENT DOCUMENTS

| 8,492,150 B2 | 7/2013 | Parker et al. |
| 8,748,181 B2 | 6/2014 | Kuo et al. |
| 8,999,378 B2 | 4/2015 | Parker et al. |
| 9,012,172 B2 | 4/2015 | Parker et al. |
| 9,068,168 B2 | 6/2015 | Feinberg et al. |
| 9,383,350 B2 | 7/2016 | Parker et al. |
| 2004/0009566 A1 | 1/2004 | Okano et al. |
| 2004/0078090 A1 | 4/2004 | Binette et al. |
| 2004/0101819 A1 | 5/2004 | Montemagno et al. |
| 2005/0080402 A1 | 4/2005 | Santamore et al. |
| 2005/0085847 A1 | 4/2005 | Galdonik et al. |
| 2006/0003439 A1 | 1/2006 | Ismagilov et al. |
| 2007/0060815 A1 | 3/2007 | Martin et al. |
| 2010/0196432 A1 | 8/2010 | Feinberg et al. |
| 2011/0189719 A1 | 8/2011 | Kuo et al. |
| 2011/0250585 A1 | 10/2011 | Ingber et al. |
| 2012/0134570 A1 | 5/2012 | Trumbull et al. |
| 2012/0135448 A1 | 5/2012 | Parker et al. |
| 2012/0142556 A1* | 6/2012 | Parker ............... G01N 33/5061 506/10 |
| 2013/0046134 A1 | 2/2013 | Parker et al. |
| 2013/0312638 A1 | 11/2013 | Parker et al. |
| 2013/0330378 A1 | 12/2013 | Parker et al. |
| 2014/0236267 A1 | 8/2014 | Parker |
| 2014/0322515 A1 | 10/2014 | Parker et al. |
| 2015/0182679 A1 | 7/2015 | Parker et al. |
| 2015/0253307 A1 | 9/2015 | Parker et al. |
| 2015/0354094 A1 | 12/2015 | Parker et al. |
| 2016/0003806 A1 | 1/2016 | Parker et al. |

FOREIGN PATENT DOCUMENTS

| WO | WO-2012/131360 A2 | 10/2012 |
| WO | WO-2013/086512 A2 | 6/2013 |
| WO | WO-2013/115896 A2 | 8/2013 |
| WO | WO-2016/007879 A1 | 1/2016 |
| WO | WO-2016/069142 A2 | 5/2016 |
| WO | WO-2016/191179 A1 | 12/2016 |
| WO | WO-2017/027390 A1 | 2/2017 |
| WO | WO-2017/087759 A1 | 5/2017 |
| WO | WO-2018/027105 A1 | 2/2018 |

OTHER PUBLICATIONS

Ahmad Atieh "Design, Modeling, Fabrication and Testing of a Piezoresistive-Based Tactile Sensor for Minimally Invasive Surgery Applications" Master of Applied Science in Mechanical Engineering at Concordia University, Montreal, Quebec, Canada., Feb. 2012 (Year: 2012).*
NDT Resource Center "Stress and Strain" 3 pgs., available online Oct. 18, 2014 (Year: 2014).*
Jung et al. "Traction Force of Smooth Muscle Cell During Growth on a Rigid Substrate" MEMS 2014, San Francisco, CA, USA, Jan. 26-30, 2014, pp. 290-293 (Year: 2014).*
Alford et al., "Biohybrid thin films for measuring contractility in engineered cardiovascular muscle" *Biomaterials* 31, May 2010, 3613-3621.
Badrossamay, M.R. et al. "Nanofiber assembly by rotary jet-spinning." Nano Letters, May 2010;10(6):2257-2261.

(Continued)

*Primary Examiner* — Thane Underdahl
(74) *Attorney, Agent, or Firm* — McCarter & English, LLP; Maria Laccotripe Zacharakis; Anita M. Bowles

(57) ABSTRACT

Embodiments described herein are directed to devices for supporting growth of anisotropic muscle tissue layers and in vitro readout and quantification of force generated by the tissue layers using one or more strain-sensing elements integrated into the device. Embodiments also include multiplexed apparatuses of multiple independent devices, methods of fabricating the devices and apparatuses, and methods of using the devices and apparatuses.

14 Claims, 20 Drawing Sheets

(56) References Cited

OTHER PUBLICATIONS

Bray et al., "Sarcomere Alignment is Regulated by Myocyte Shape" *Cell Motility and the Cytoskeleton*, Aug. 2008, 65(8), pp. 641-651.

Bursac et al., "Cardiomyocyte cultures with controlled macroscopic anisotropy." *Circulation Rearch*, Dec. 2002, vol. 91, pp. e45-e54.

Grosberg et al., "Ensembles of engineered cardiac tissues for physiological and pharmacological study: Heart on a chip." Lab Chip, Nov. 2011, vol. 11, p. 4165.

Lehnert et al., "Cell behavior on micropatterned substrata: limits of extracellular matrix geometry for spreading and adhesion." *Journal of Cell Science*, Jan. 2004, vol. 117 (1), pp. 41-52.

Mao et al., "Capillary isoelectric focusing with whole col. imaging detection for analysis of proteins and peptides," J. Biochem. Biophys. Methods, Feb. 1999, 39:93-110.

Park et al., "Real-Time Measurement of the Contractile Forces of Self-Organized Cardiomyocytes on Hybrid Biopolymer Microcantilevers," Anal. Chem. Oct. 2005, 77:6571-6580.

Parker et al., "Extracellular matrix, mechanotransduction and structural hierarchies in heart tissue engineering." Phil Trans R. Soc B, Epub, Jun. 22, 2007, vol. 362, pp. 1267-1279.

Spring, Kenneth R. "Electronic Imaging in Neuroscience," Curr. Protoc. Neurosci. May 2002, 2.4.1-2.4.9.

Xi et al., "Development of a Self-Assembled Muscle-Powered Piezoelectric Microgenerator", NSTI-Nanotech, 2004, vol. 1, pp. 3-6. (The month of publication is not available; however, the year of publication is sufficiently earlier than the effective U.S. filed and any foreign priority date so that the particular month of publication is not in issue.).

Yang et al., "Fabrication of well-defined PLGA scaffolds using novel microembossing and carbon dioxide bonding," Biomaterials, Sep. 2005, vol. 26, pp. 2585-2594.

U.S. Appl. No. 12/443,890, filed Apr. 8, 2010, US 20100196432, Abandoned.

U.S. Appl. No. 12/223,560 U.S. Pat. No. 8,492,150, filed Feb. 25, 2009, US 20090317852, Granted.

U.S. Appl. No. 13/922,432 U.S. Pat. No. 9,383,350, filed Jun. 20, 2013, US 20140004553, Granted.

U.S. Appl. No. 12/680,277 U.S. Pat. No. 9,068,168, filed Sep. 1, 2010, US 20100330644, Granted.

U.S. Appl. No. 12/994,187 U.S. Pat. No. 8,748,181, filed Mar. 17, 2011, US 20110189719, Granted.

U.S. Appl. No. 13/120,003 U.S. Pat. No. 8,999,378, filed Jun. 2, 2011, US 20120029416, Granted.

U.S. Appl. No. 13/878,383, filed Aug. 16, 2013, US 20130330378, Abandoned.

U.S. Appl. No. 13/318,227 U.S. Pat. No. 9,012,172, filed Feb. 21, 2012, US 20120142556, Granted.

U.S. Appl. No. 14/642,906, filed Mar. 10, 2015, US 20160003806, Published.

U.S. Appl. No. 13/320,031, filed Jan. 30, 2012, US 20120135448, Granted.

U.S. Appl. No. 15/203,924, filed Jul. 7, 2016, Abandoned.

U.S. Appl. No. 13/580,191, filed Oct. 31, 2012, US 20130046134, Abandoned.

U.S. Appl. No. 13/808,411, filed Jan. 4, 2013, Abandoned.

U.S. Appl. No. 14/261,693, filed Apr. 25, 2014, US 20140236267, Published.

U.S. Appl. No. 13/988,088, filed Aug. 5, 2013, US 20130312638, Abandoned.

U.S. Appl. No. 14/362,287, filed Jun. 2, 2014, US 20140342394, Published.

U.S. Appl. No. 14/359,005, filed May 16, 2014, US 20140322515, Published.

U.S. Appl. No. 14/415,945, filed Jan. 20, 2015, US 20150182679, Allowed.

U.S. Appl. No. 14/429,826, filed Mar. 20, 2015, US 20150253307, Abandoned.

U.S. Appl. No. 15/869,228, filed Jan. 12, 2018, Pending.

U.S. Appl. No. 14/763,620, filed Jul. 27, 2015, US 20150354094, Published.

PCT/US2015/039983, Jul. 10, 2015, WO 2016007879, Published.

PCT/US2015/051818, Sep. 24, 2015, WO 2016069142, Published.

PCT/US2016/033168, May 19, 2016, WO 2016191179, Published.

PCT/US2016/045813, Aug. 5, 2016, Pending.

PCT/US2016/062693, Nov. 18, 2016, WO 2017/087759, Published.

PCT/US2017/045442, Aug. 4, 2017, WO 2018/027105, Published.

International Search Report and Written Opinion from PCT/US2015/016395, dated Jan. 6, 2016 pp. 1-16.

\* cited by examiner

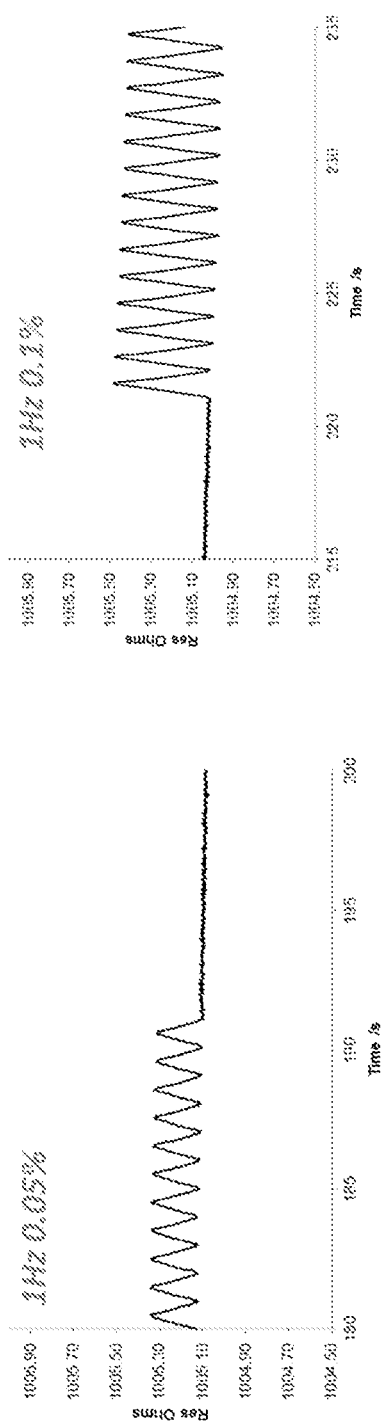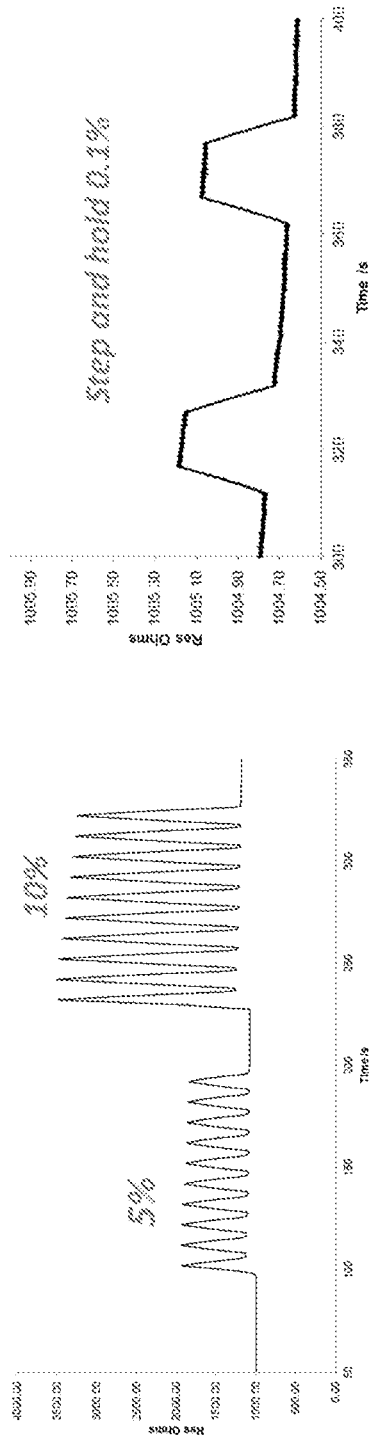
Figure 11A  Figure 11B  Figure 11C  Figure 11D

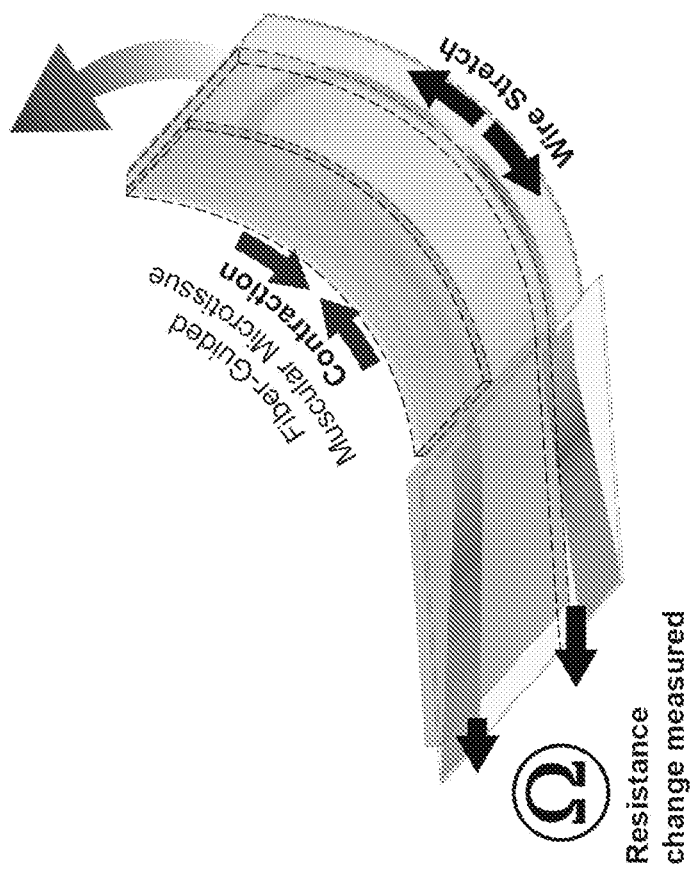
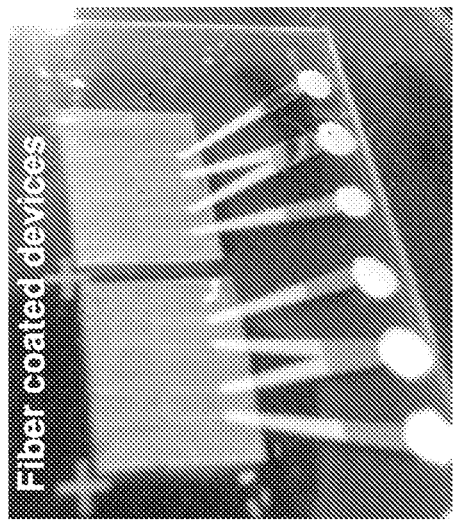
Figure 14A
Figure 14B

PCL:gelatin pull spun fiber sheet

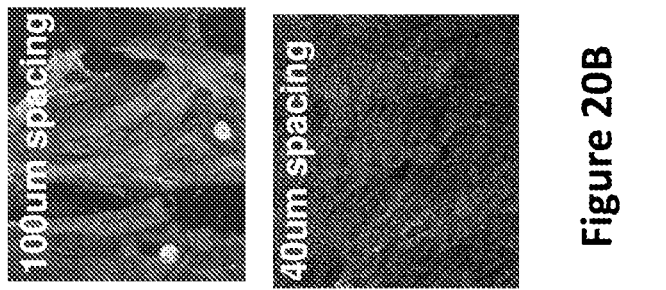
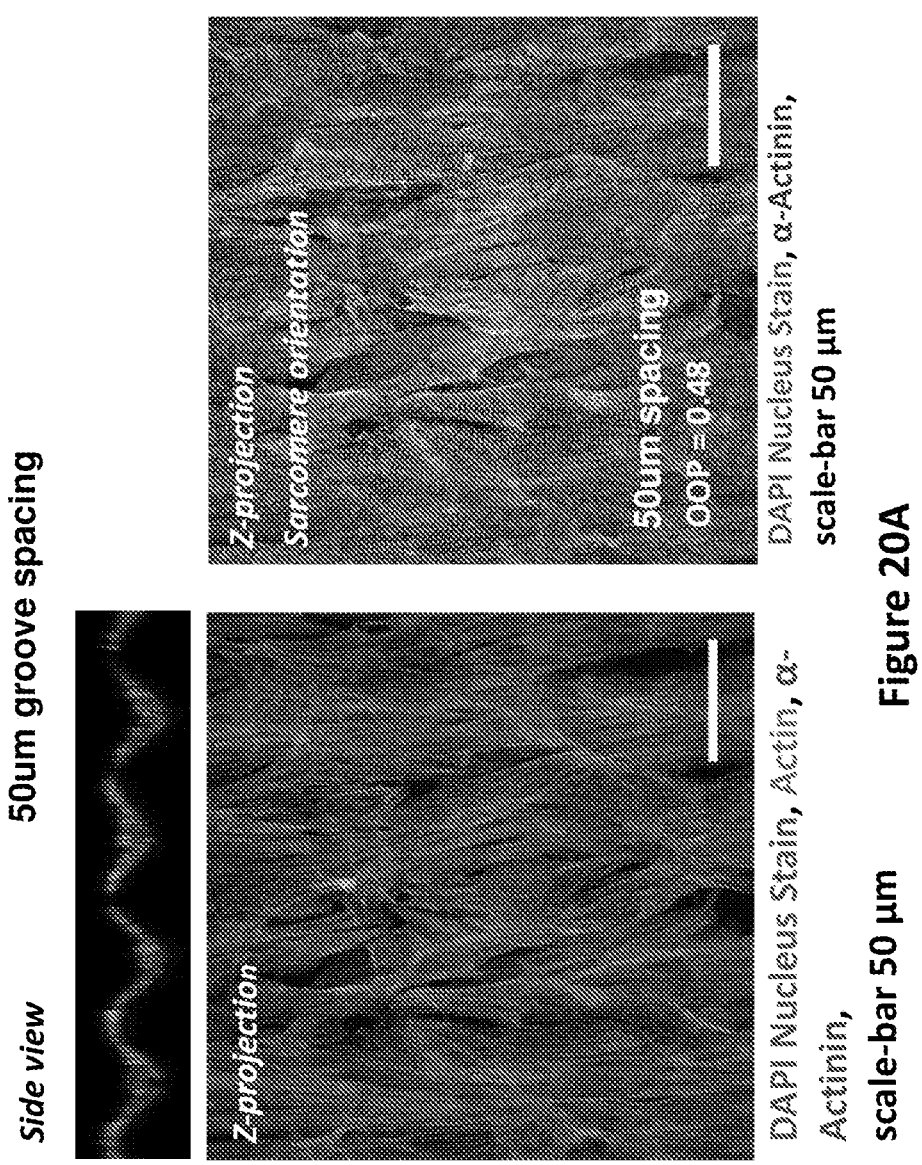
Figure 20B
Figure 20A

ANISOTROPIC MUSCULAR TISSUE DEVICES WITH INTEGRATED ELECTRICAL FORCE READOUTS

RELATED APPLICATIONS

This application is a 35 U.S.C. § 371 national stage filing of International Application No. PCT/US2015/016395, filed on Feb. 18, 2015, which in turn claims priority to U.S. Provisional Application No. 61/941,119, filed Feb. 18, 2014. The entire contents of each of the foregoing applications are incorporated herein by reference.

GOVERNMENT INTEREST

This invention was made with government support under grant number W911NF-12-2-0036, awarded by the Defense Advanced Research Projects Agency (DARPA), and under grant number 3UH2TR000522-02S1, awarded by the National Institutes of Health (NIH). The government has certain rights in the invention.

BACKGROUND OF THE INVENTION

Muscle thin films (MTFs) and devices comprising MTFs include functional muscle tissue (e.g., muscle tissue comprising anisotropically aligned muscle cells which contract as a single unit). Current devices comprising MTFs rely on relatively data-heavy and low throughput optical microscopy-based techniques for measuring the contractile force generated by the muscle tissue. This may limit their value for high throughput biomedical studies.

SUMMARY

In one aspect, the present invention provides devices for measuring a contractile function of a muscle tissue layer in vitro. The devices include a flexible substrate including a first polymer substrate layer, one or more strain-sensitive electrical elements, and a second polymer substrate layer at least partially overlying the one or more strain-sensitive electrical elements and a tissue supporting layer on the flexible substrate configured to promote adherence and in growth of muscle cells, one or both of the flexible substrate and the tissue supporting layer configured for anisotropic growth of muscle tissue to form an anisotropic muscle tissue layer that can perform a contractile function adhered to the flexible substrate.

The one or more strain-sensitive electrical elements may be configured to change resistance in response to strain from contraction of the muscle tissue layer, or generate a voltage in response to strain from contraction of the muscle tissue layer.

In one embodiment, a capacitance of the one or more strain-sensitive electrical elements changes in response to strain from contraction of the anisotropic muscle tissue layer.

In one embodiment, the device is configured to exhibit out of plane deflection in response to force applied by the muscle tissue layer, e.g., a first end of the flexible substrate is fixed and a second end of the flexible substrate is free forming a cantilever.

In one embodiment, the device is configured to exhibit measureable in-plane strain in response to force applied by the muscle tissue layer. The effective modulus of the flexible substrate in a deformation zone may be in the range of 1 kPa to 100 kPa and the tissue supporting layer is configured to support muscle tissue having a thickness of one to two cells, or the effective modulus of the flexible substrate in the deformation zone may be in the range of 1 kPa to 1 MPa and the tissue supporting layer comprises a scaffold configured to support muscle tissue having a thickness of between 1 micron and 100 microns.

In one embodiment, the flexible substrate further comprises a hydrogel layer, e.g., gelatin, overlying the second polymer layer.

In one embodiment the one or more strain-sensitive electrical elements comprises a wire, such as a wire comprising a thin film of gold on a thin film of titanium or a thin film of gold on a thin film of chromium. In one embodiment, the wire is piezoresistive. In another embodiment, the wire comprises a thin film of gold on a thin film of titanium, the thin film of titanium has a thickness of 0.5 nm to 4 nm, and the flexible substrate comprises a polymer, e.g., polydimethylsiloxane. In one embodiment, the thin film of gold on a thin film of titanium is a microcracked, continuous, stress-relieved titanium-gold film.

In one embodiment, the one or more strain-sensitive electrical elements comprise particles embedded in the flexible substrate, such as piezoelectric particles, conductive particles, carbon particles, or silver particles.

In one embodiment, the one or more strain-sensitive electrical elements comprise a wire including conductive particles. In another embodiment, the one or more strain-sensitive electrical elements comprise a wire based on a composite of conductive particles and a support material.

In one embodiment, the one or more strain-sensitive elements comprise a wire including a conductive polymer, such as a polymer wire doped with conductive particles, e.g., carbon particles or silver particles. In one embodiment, the polymer wire comprises polyamide.

In one embodiment, the tissue supporting layer comprises a micro-patterned layer of chemical cues to chemically direct anisotropic muscle tissue growth.

In one embodiment, a surface of the flexible substrate has a micro-patterned shape to structurally direct anisotropic muscle tissue growth. The micro-patterned shape may promote growth of a muscle tissue layer with portions having a thickness of more than a monolayer of cells, or the micro-patterned shape may comprise a microgrooved structure of hills and valleys with a hill to hill spacing in the range of 3 microns to 100 microns, or the micro-patterned shape may comprise a microgrooved structure of hills and valleys with a hill to hill spacing in the range of 45 microns to 65 microns. The hill to valley height may be in the range of 3 microns to 100 microns, or in the range of 5 microns to 30 microns.

In one embodiment, the tissue supporting layer has a micro-patterned shape to structurally direct anisotropic muscle tissue growth.

In one embodiment, the tissue supporting layer comprises a plurality of micron, submicron and/or nanometer diameter fibers oriented substantially in the same direction to structurally direct anisotropic muscle tissue growth. The plurality of micron, submicron and/or nanometer diameter fibers may form a sheet of fibers having a thickness in the range of 2 microns to 20 microns, or a sheet of fibers having a thickness in the range of 20 microns to 200 microns. In one embodiment, the plurality of micron, submicron and/or nanometer diameter fibers in the sheet of fibers are configured to form scaffold for cellular growth. The devices of the invention may further comprise an anisotropic muscle tissue layer on the tissue supporting layer and adhered to the flexible substrate.

The devices of the invention may also further comprise a rigid holder to which at least one end of the flexible substrate is attached.

The rigid holder may further comprise a well for containing a tissue growth medium, leads connected to the strain-sensitive electrical elements. In one embodiment, the strain-sensitive electrical elements are piezoresistive elements. In one embodiment, the strain-sensitive electrical elements and leads form half of a Wheatstone bridge.

In one embodiment, the devices of the invention are microfluidics device, and further comprise a rigid body having an inlet and an outlet, at least one end of the flexible substrate attached to the rigid body.

In one aspect, the present invention provides apparatuses for measuring contractile function of multiple muscular tissue layers. The, the apparatuses include a rigid holder; and a plurality of devices of the invention, at least one end of the flexible substrate of each device is independently attached to the rigid base.

The rigid holder may comprise a plurality of electrical leads independently connected to the strain-sensitive electrical elements for each device, or a plurality of wells associated with the plurality of devices, each well independently configured to contain a growth medium for the associated device.

In one embodiment, the apparatus includes one or more microfluidic channels associated with the plurality of devices.

In another aspect, the present invention provides methods of making a device for measuring a contractile function of a muscle tissue layer. The methods include forming a sacrificial polymer layer on a rigid base material, disposing a flexible substrate including one or more strain-sensitive electrical elements on the rigid base material, at least a portion of the flexible substrate overlaying the sacrificial polymer, wherein disposing the flexible substrate including one or more strain-sensitive electrical elements on the rigid base material includes depositing a first polymer substrate layer on the sacrificial polymer layer, disposing the one or more strain-sensitive electrical elements on the first polymer substrate layer, and depositing a second polymer substrate layer on the first polymer substrate layer and on the one or more strain-sensitive electrical elements, disposing a tissue supporting layer on the flexible substrate, the tissue supporting layer configured to promote adherence and in growth of muscle cells, one or both of the flexible substrate and the tissue supporting layer configured for anisotropic growth of muscle tissue to form an anisotropic muscular tissue layer that can perform a contractile function adhered to the flexible substrate, and removing the sacrificial polymer layer to free at least a portion of the flexible substrate from the underlying rigid base material.

The sacrificial polymer layer may be removed after the tissue supporting layer is disposed on the flexible substrate, or prior to disposing the tissue supporting layer on the flexible substrate.

In one embodiment, disposing the one or more strain-sensitive electrical elements on the first polymer substrate layer comprises forming a wire on the first polymer substrate layer.

In one embodiment, forming a wire on the first polymer substrate layer includes depositing a patterned titanium or chromium adhesion layer on the first polymer substrate layer, depositing a patterned gold layer on the patterned titanium or chromium adhesion layer; and annealing to relax stresses in the patterned titanium or chromium adhesion layer, in the patterned gold layer, and in the first polymer substrate layer, thereby forming the wire.

The titanium or chromium adhesion layer may have a thickness of 0.5 nm to 4 nm and the first polymer substrate layer has a thickness of 0.5 microns to 70 microns, or the titanium or chromium adhesion layer may have a thickness of 4 nm to 10 nm and the first polymer substrate layer has a thickness of 70 microns to 100 microns.

In one embodiment, the titanium or chromium adhesion layer and the gold layer are deposited by thermal evaporation or e-beam evaporation.

In one embodiment, the resulting wire is a piezoresistive wire that can stretch by at least 10% without failure.

In one embodiment, the first polymer layer comprises polydimethylsiloxane.

In one embodiment, forming a wire on the first polymer substrate layer comprises depositing a patterned polymer doped with micron-to-nanometer sized conducting particles on the first polymer substrate layer.

In another embodiment, forming a wire on the first polymer substrate layer comprises depositing a patterned conductive polymer on the first polymer substrate.

In one embodiment, depositing the first polymer substrate layer comprises direct ink writing a first polymer substrate layer on the rigid substrate and the sacrificial layer; wherein forming the wire on the first polymer substrate comprises direct ink writing a patterned conductive layer on the first polymer substrate layer; wherein depositing the second polymer substrate layer on the first polymer substrate layer and on the wire comprises direct ink writing the second polymer layer.

In one embodiment, the direct ink writing the patterned conductive layer on the first polymer substrate layer comprises direct ink writing a polymer doped with conductive particles on the first polymer substrate layer.

In one embodiment, the methods further comprise forming leads to the wire on the first polymer substrate by direct ink writing a patterned silver particle doped polyamide layer on the first polymer substrate prior to depositing the second polymer substrate layer on the wire.

The methods of the invention may further comprise creating a microgrooved structure of hills and valleys on a top surface of the second polymer substrate layer.

In one embodiment, depositing the second polymer substrate layer on the first polymer substrate layer and on the wire comprises direct ink writing the second polymer layer and direct ink writing a microgrooved structure of hills and valleys onto at least a portion of a top surface of the second polymer substrate layer. The microgrooves may have a hill to hill spacing in the range of 1 micron to 200 microns, or a hill to hill spacing in the range of 45 microns to 65 microns. The microgrooves may have a hill to valley height in the range of 3 microns to 100 microns, or a hill to valley height in the range of 5 microns to 30 microns.

In one embodiment, disposing the flexible substrate including one or more strain-sensitive electrical elements on the rigid base material further comprises depositing a hydrogel layer, e.g., gelatin, on the second polymer substrate layer.

In one embodiment, the second polymer substrate has a top surface with micro-patterned shape to structurally direct anisotropic muscle tissue growth.

In one embodiment, disposing the tissue supporting layer on the flexible substrate comprises depositing an micro-patterned layer of chemical cues to chemically direct anisotropic muscle tissue growth on the flexible substrate.

In one embodiment, the tissue supporting layer comprises a plurality of micron, submicron and/or nanometer diameter fibers all oriented in substantially the same direction to structurally direct anisotropic tissue growth.

The plurality of micron, submicron and/or nanometer diameter fibers form a sheet of fibers having a thickness in the range of 2 microns to 200 microns, or a sheet of fibers having a thickness in the range of 20 microns to 100 microns.

The methods of the invention may further comprise producing the oriented micron, submicron and/or nanometer diameter fibers by rotary jet spinning or pull spinning.

The methods of the invention may also further comprise seeding the tissue supporting layer with muscle cells and growing an anisotropic muscle tissue layer on the tissue supporting layer.

In one aspect, the present invention provides methods of measuring a contractile function of a muscle tissue. The methods include providing a muscle tissue layer device including a muscle tissue layer adhered to an underlying flexible substrate having integrated electrical sensing of strain in the flexible substrate; and measuring a strain in the flexible substrate using the integrated electrical strain-sensing and relating the measured strain to a force exerted on the flexible substrate by the muscle tissue layer, e.g., a device of the invention.

In one embodiment measuring the strain comprises measuring a change in resistance of one or more strain-sensitive electrical elements in the flexible substrate.

The one or more strain-sensitive electrical elements may comprise piezoresistive elements, or strain gauge elements.

In one embodiment, measuring the strain comprises measuring a voltage generated by one or more strain-sensitive electrical elements in the flexible substrate.

In one embodiment, the one or more strain-sensitive electrical elements comprise piezoelectric elements. In one embodiment, the one or more piezoelectric elements are embedded in the flexible substrate.

In one embodiment, the one or more strain-sensitive electrical elements comprise wires embedded in the flexible substrate. In another embodiment, the one or more strain-sensitive electrical elements comprise particles embedded in the flexible substrate.

In one embodiment, the flexible substrate further comprises a hydrogel layer overlying the second polymer substrate layer.

In one embodiment, force applied by the muscle thin film causes strain in the flexible substrate through out of plane bending of the flexible polymer.

In one embodiment, a first end of the flexible substrate is fixed and a second end of the flexible substrate is free forming a cantilever or beam.

In another embodiment, force applied by the muscle thin film causes in plane strain in the flexible substrate.

The effective modulus of the flexible substrate in a deformation zone may be in the range of between 1 kPa and 100 kPa and the muscle tissue layer has a thickness of one to two cells, or the effective modulus of the flexible substrate in a deformation zone may be in the range of 1 kPa to 1 MPa and the muscle tissue has a thickness of between 10 microns and 100 microns.

The methods of the invention may further comprise applying a stimulus to the muscle tissue layer, contacting the muscle tissue layer with a candidate compound, and comparing a first time-dependent strain in the presence of the candidate compound to a second time-dependent strain in the absence of the candidate compound, wherein a difference between the first time-dependent strain and the second time-dependent strain indicates that the candidate compound modulates contractile function of muscle tissue.

In another aspect, the present invention provides methods of measuring contractile function of muscle tissue. The methods include providing an apparatus of the invention wherein each device in the apparatus further comprises an anisotropic muscle tissue layer grown on the tissue supporting layer and adhered to the flexible substrate, and for each device in the apparatus, independently measuring a strain in the flexible substrate using the one or more strain-sensitive electrical elements and relating the measured strain to a force exerted on the flexible substrate by the muscle tissue layer.

The methods may further include applying a stimulus to the muscle tissue layer of at least one of the plurality of devices, contacting the muscle tissue layer with a candidate compound, and comparing a first time-dependent strain in the muscle tissue of the at least one of the plurality of devices in the presence of the candidate compound to a second time-dependent strain in the same muscle tissue layer in the absence of the candidate compound or in a muscle tissue layer of a different device in the absence of the candidate compound, wherein a difference between the first time-dependent strain and the second time-dependent strain indicates that the candidate compound modulates contractile function of muscle tissue.

The methods may also further comprise changing an environment to which the muscle tissue layer is exposed, and measuring a second strain in the flexible substrate while the muscle tissue layer is exposed to the changed environment using the integrated electrical strain-sensing and relating the second measured strain to a second force exerted on the flexible substrate by the muscle tissue layer when exposed to the changed environment.

BRIEF DESCRIPTION OF THE DRAWINGS

FIG. 11A is a graph of resistance change as a function of time for a 3 nm thick Ti, 20 nm thick Au, 1 nm thick Ti wire undergoing a cyclic 0.05% strain at a frequency of 1 Hz.

FIG. 11B is a graph of resistance change as a function of time for the wire undergoing a cyclic 0.1% strain at a frequency of 1 Hz.

FIG. 11C is a graph of resistance change as a function of time for the wire undergoing a cyclic 5% strain and a cyclic 10% strain at a frequency of about 0.1 Hz.

FIG. 11D is a graph of resistance change as a function of time for the wire undergoing step and hold cycles of 0.1% strain.

FIG. 14A schematically depicts a device with piezoresistive sensing and a tissue supporting layer including a fiber construct, in accordance with some embodiments.

FIG. 14B is an image of devices according to the design of FIG. 14A.

FIG. 20A includes confocal images of immunostained anisotropic tissue on a microgrooved structure with a groove spacing of 50 μm showing desirable anisotropic tissue development.

FIG. 20B includes confocal images of immunostained anisotropic tissue on microgrooved structures with groove spacings of 40 μm and 100 μm.

DETAILED DESCRIPTION OF INVENTION

Figure 1A:
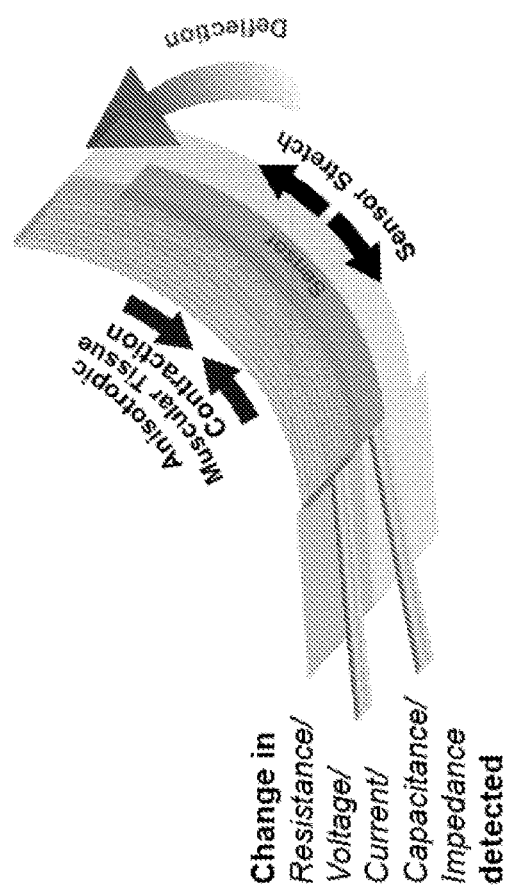
FIG. 1A schematically depicts a device for electrically measuring contractile function of a muscle tissue layer employing out of plane deflection of a flexible substrate in a cantilever geometry, in accordance with an embodiment.

Embodiments of the present invention are directed to devices for growth and in vitro measurements of functional muscle tissue layers that are effective and more efficient for, for example, high throughput assays, multiplexed apparatuses including such devices, methods of making such devices and apparatuses, and methods of using such devices and apparatuses. Examples of the integration of strain-sensitive elements into devices that support adhered muscle tissue layers to allow electronic readout and quantification of the force generated by the muscle tissue are described. Such in-line electrical force sensing enables devices including muscle tissues to serve as mass producible, high throughput models for biomedical and pharmaceutical studies.

Embodiments and examples described herein provide devices that support growth of physiologically relevant anisotropic muscle tissue in vitro, and include integrated electrical force sensors to allow electronic readout and quantification of the force generated by the tissue. Embodiments and examples described herein further provide devices and apparatuses for use in high throughput platforms for biomedical and pharmaceutical studies regarding the function of muscle tissue. Such devices enable high throughput screening, as well as long-term studies inside controlled incubator environments, which may include recapitulating physiologic extremes, such as hypoxic conditions.

These muscle tissue layers are electrically functional and actively contractile, generating stresses comparable to those produced by whole papillary muscle, and the muscle tissue can be used to measure effects on muscle cell contractile function in vitro during electrical and pharmacological stimulation.

The electrical readout employed by devices described herein further facilitates multiplexing of devices into multi-well format apparatuses including micro-titer plate formats and enables force sensing without need for optical recordings, thereby allow integration into microfluidic devices and enclosed recording setups.

Some embodiments described herein provide a device for electrically measuring a contractile function of a muscle tissue layer. The device includes a flexible substrate that incorporates one or more strain-sensitive electrical elements and a tissue supporting layer on the flexible substrate configured to promote adherence and ingrowth of muscle cells. One or both of the flexible substrate and the tissue supporting layer are configured for anisotropic growth of muscle tissue to form an anisotropic tissue layer that can perform a contractile function adhered to the flexible substrate. Contraction of the muscle tissue layer causes strain in the flexible substrate and in the strain-sensitive electrical elements. If the mechanical properties of the flexible substrate are known, the contractile force exerted by the muscle tissue can be determined based on the strain measured in the flexible substrate.

Devices described herein employ two different types of geometries for generation of strain in the flexible substrate. In the first type of geometry, the flexible substrate is supported at one end and free to deflect at the opposite end (e.g., like a cantilever). Contractile forces in the muscle tissue cause bending and out of plane deflection of the free end of the flexible substrate, which, in turn, causes strain in the flexible substrate that can be measured by the strain-sensitive electrical elements. In the second type of geometry, the flexible substrate is supported at both ends and the flexible substrate maintains a flat (not deflected) geometry. Given a flexible substrate with a sufficiently low modulus of elasticity, contractile forces in the muscle tissue cause measurable in-plane strain in the flexible substrate that can be measured by the strain-sensitive electrical elements.

Figure 1B:
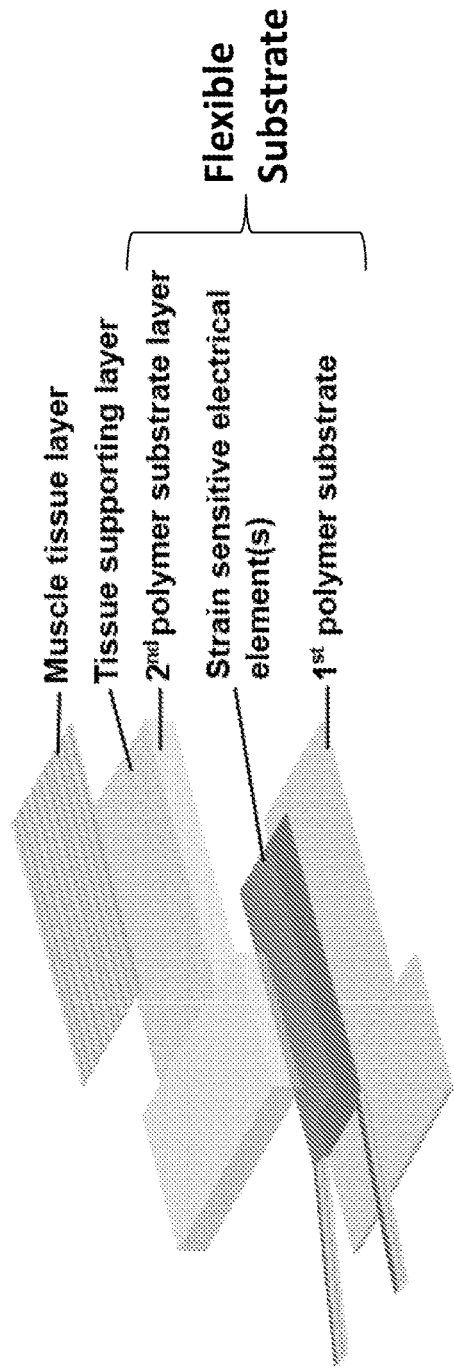
FIG. 1B schematically depicts an exploded perspective view of the device of FIG. 1A.

FIGS. 1A and 1B schematically depict a device for measuring a contractile function of a muscle tissue layer in vitro that employs the first type of geometry in accordance with some embodiments. The device includes a flexible substrate including one or more strain-sensitive electrical elements. As shown in the exploded view of FIG. 1B, the flexible substrate can include a first polymer substrate layer, one or more strain-sensitive electrical elements, and a second polymer substrate layer at least partially overlying the one or more strain-sensitive electrical elements, in accordance with some embodiments. In some embodiments, the flexible substrate may also include a hydrogel layer (e.g., gelatin) over the second polymer substrate layer.

The device also includes a tissue supporting layer on the flexible substrate. The tissue supporting layer is configured to promote adherence and in growth of muscle cells. Further details regarding the tissue supporting layer and different configurations for the tissue supporting layer are described below with respect to Examples 1-3. One or both of the flexible substrate and the tissue supporting layer are configured for anisotropic growth of muscle tissue to form an anisotropic muscle tissue layer that can perform a contractile function adhered to the flexible substrate. Configuring the tissue supporting layer to achieve growth of an anisotropic muscle tissue layer is described below with respect to Example 1 and Example 2. Configuring the flexible support layer to achieve growth of an anisotropic muscle tissue layer is described below with respect to Example 3. In some embodiments, the device is provided without the muscle tissue layer and a user may seed the tissue supporting layer with cells, incubate the device, and grow the muscle tissue layer. In other embodiments, the device may be provided with the muscle tissue layer already grown.

FIG. 1A schematically illustrates how contraction of the anisotropic muscular tissue layer causes out of plane deflection at the free end of the flexible substrate. A contractile force in the muscle tissue layer causes the flexible substrate to bend in order to accommodate the stress created in the top muscle tissue layer. This bending causes different strains in different levels of the flexible substrate (e.g., a stretching strain in the lower portion of the flexible substrate and a compressive strain in the upper portion of the flexible substrate). The strain sensitive element detects the strain present in the level of the flexible substrate in which it is located (e.g., the strain in the portion of the thickness of the device in which it is located). The one or more strain-sensitive elements may produce a change in resistance, a generated voltage, a change in current, a change in capacitance, or a change in impedance based on strain in the device. The degree of bending in the flexible substrate, and the corresponding strain in the strain-sensitive electrical element, in response to the stress applied by the contracting muscle film layer depends on the thickness of the flexible substrate, the position of the strain-sensitive electrical element in the thickness of the flexible substrate, and the composite modulus of elasticity of the flexible substrate. For devices with the cantilever geometry, the acceptable range for the composite modulus of elasticity flexible substrate is relatively large (e.g., 1 kPa to 100 GPa). Reductions in the thickness of the flexible substrate enable materials having a higher modulus of elasticity to be employed. To remain physiologically relevant, the modulus of elasticity of the flexible substrate should not be lowered below 1 kPa because formation of the muscle tissue layer requires the underlying substrate to have at least a certain amount of stiffness. Example 1 below details how contractile tissue stress is determined from a resistance change in a piezoresistive wire for a bending beam geometry.

Figure 2:
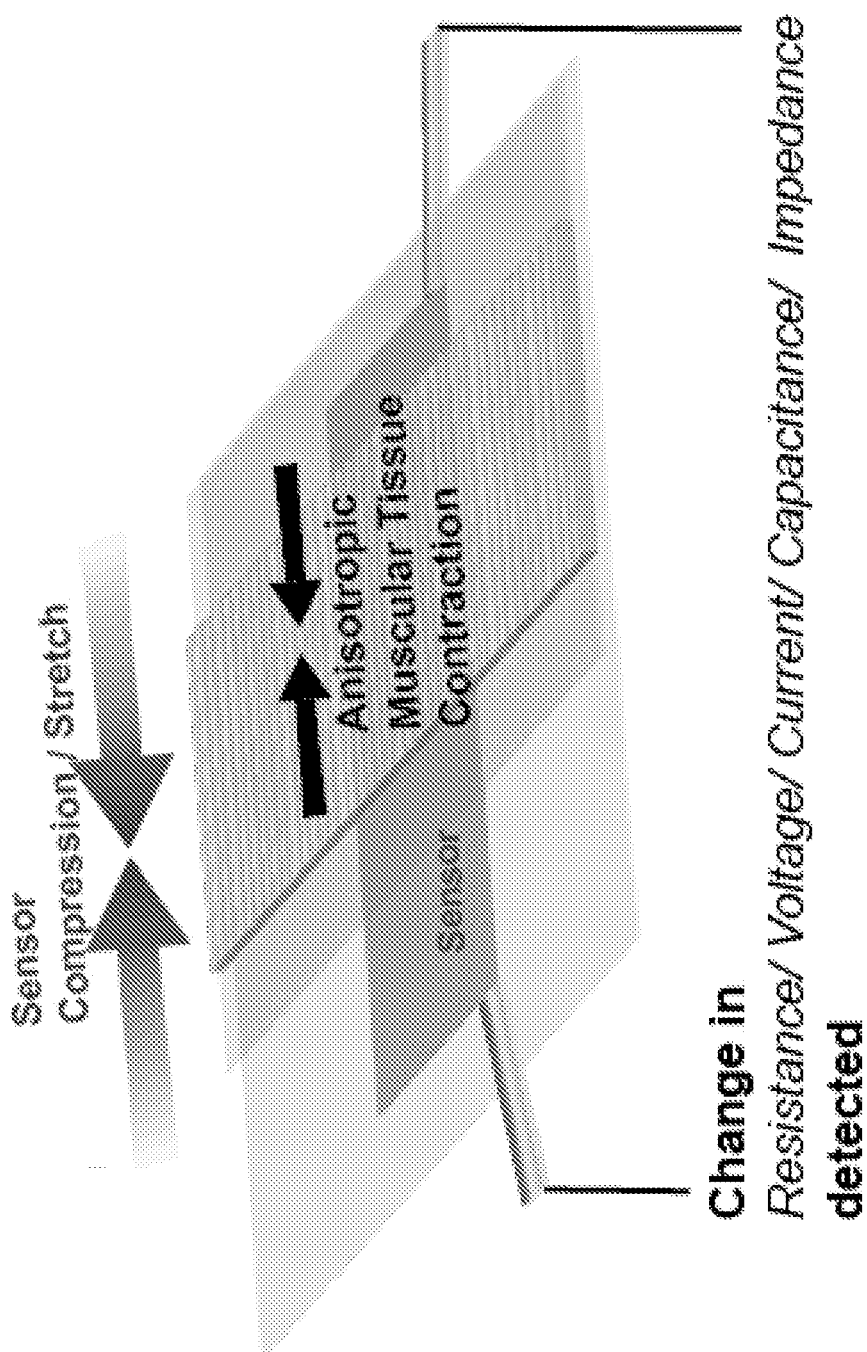
FIG. 2 schematically depicts a device for electrically measuring contractile function of a muscle tissue layer with a planar geometry for detection of in-plane strain without out of plane deflection of a flexible substrate, in accordance with an embodiment.

FIG. 2 schematically depicts the second geometry for device embodiments. In this geometry, both ends of the flexible substrate are supported or fixed, preventing or greatly reducing any out of plane bending or deflection of the flexible substrate due to contractile force in the muscle tissue layer. Instead, contractile force in the muscle tissue layer cause in-plane strain in which the ends of the muscle tissue pull toward each other. In some embodiments, flexible substrate may remain attached to an underlying rigid substrate during measurements. In these embodiments, it is important that the composite modulus of elasticity of the flexible substrate is sufficiently small such that the force generated through tissue contraction can produce a measureable in-plane strain in the flexible substrate. However, the modulus of elasticity of the flexible substrate must be sufficiently large to support to support growth of the anisotropic tissue layer. For embodiments in which the muscle tissue layer is one to two cells thick, the magnitude of the stress generated by contraction of the muscle tissue layer is in the range 1 to 100 kPa, and for the planar geometry, the effective modulus of elasticity of the flexible substrate in a deformation zone (e.g., within 50 µm of the tissue supporting layer) may be in the range of 1 kPa to 100 kPa. In embodiments in which the muscle tissue layer is more than two cells thick, the composite modulus of elasticity of the flexible substrate in the deformation can be greater because the contractile force generated by the muscle tissue layer is greater. In other embodiments, the flexible substrate may be free of an underlying rigid substrate and only supported at the ends (e.g., like a membrane). In these embodiments, the modulus of elasticity of the flexible substrate may have values similar to those of the cantilever geometry embodiments.

Figure 3A:
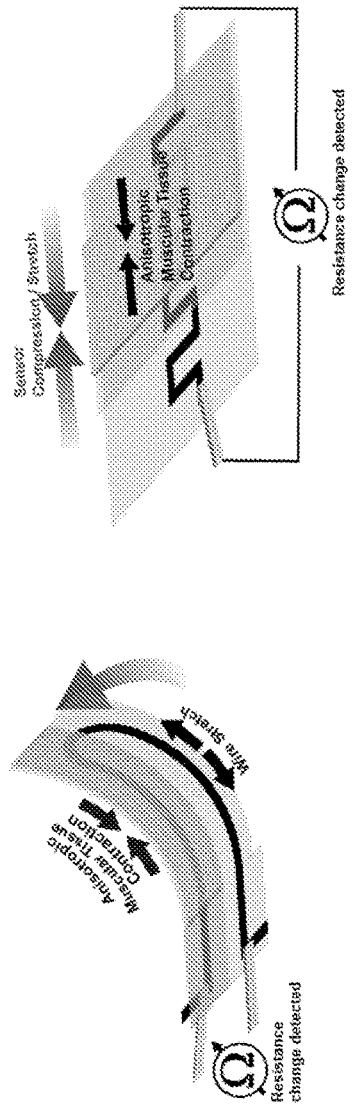
FIG. 3A schematically depicts a cantilever geometry device and a planar geometry device for electrically measuring contractile function of a muscle tissue layer through resistance changes (e.g., using piezoresistive strain sensing), in accordance with some embodiments.
Figure 3B:
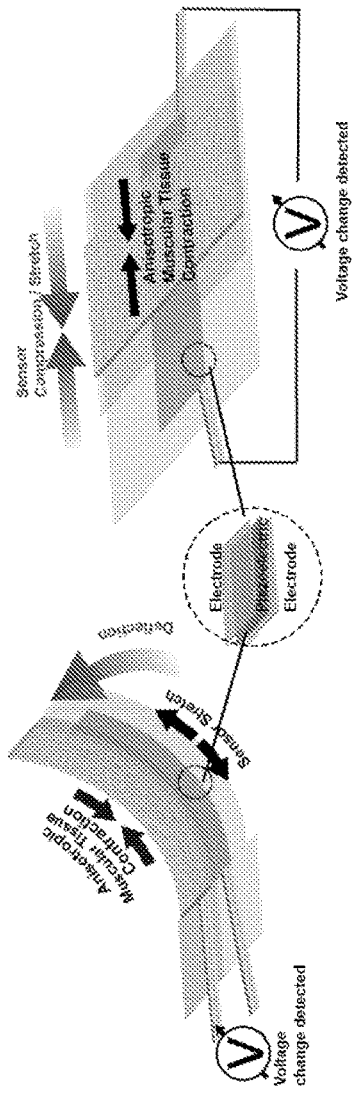
FIG. 3B schematically depicts a cantilever geometry device and a planar geometry device for electrically measuring contractile function of a muscle tissue layer through changes in generated voltage (e.g., using piezoelectric strain sensing), in accordance with some embodiments.
Figure 3C:
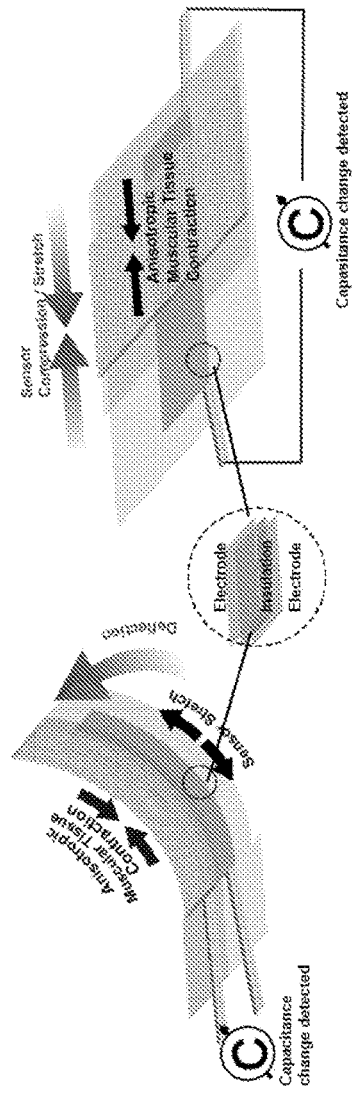
FIG. 3C schematically depicts a cantilever geometry device and a planar geometry device for electrically measuring contractile function of a muscle tissue layer through changes in capacitance (e.g., using capacitive strain sensing), in accordance with some embodiments.

As noted above, different mechanisms may be employed for electrically sensing strain in the flexible substrate as a result of contractile forces in the muscle tissue layer. FIGS. 3A-3C depict cantilever geometry devices and planar geometry devices for sensing strain produced by the muscle tissue layers using different types of electrical sensing.

In the devices depicted in FIG. 3A, piezoresistive wire is used to sense strain in the flexible substrate due to contraction in the muscle tissue layer. Change in resistance in the piezoresistive wire has a known relationship to strain in the wire, which enables strain in the wire to be determined based on measured changes in resistance in the wire. Examples of piezoresistive materials that may be employed for the piezoresistive wire include, but are not limited to: titanium-gold or chromium-gold thin films, polymer (e.g., poly-dimethylsiloxane (PDMS)) doped with conductive particles (e.g., carbon nanoparticles), and doped silicon semiconductors.

In the devices depicted in FIG. 3B, the one or more strain-sensitive elements include piezoelectric elements positioned between electrodes. Strain on the piezoelectric elements, due to contraction of the muscle tissue layer generates a voltage across the piezoelectric elements, which can be measured using the electrodes. The piezoelectric elements may be particles, wires, plates or any other suitable configuration. Examples of piezoelectric materials that may be employed include, but are not limited to: piezoelectric polymers (e.g., polyvinylidene fluoride (PVDF), polyvinyledenedifluoride-trifluoroethylene (PVDF-TrFe) co-polymers), inorganic piezoelectric materials (e.g., zinc oxide (ZnO) and lead zirconium titanate (PZT)), and composites based on either class of materials. Any suitable conductive material may be used for the electrodes.

In the devices depicted in FIG. 3C, the one or more strain-sensitive elements include electrodes separated by an insulator forming a capacitor. The contraction of the muscle tissue layer causes both in-plane strain in the flexible substrate and an out of plane strain in the flexible substrate that changes the spacing of the electrodes, which changes the measured capacitance across the electrodes. This change in capacitance can be related to the out of plain strain, which, in turn, can be related to the stress and force generated by the muscle tissue layer. Any suitable conductive material may be used for the electrodes. Any suitable insulating materials may be used for the insulator.

Types of integrated electrical sensors that may be employed as strain-sensitive elements in devices to detect contractile stress in muscle tissues include, but are not limited to: strain gauges, piezoresistive sensors, piezoelectric sensors, sensors based on changes in capacitance, and sensors based on inductance. These can be combined with integrated electrical recording of tissue action potential and propagation, e.g., through flexible micro-electrode arrays integrated directly below the tissue support layer.

Many different materials may be employed for strain-sensing elements and leads or contacts for the strain-sensing elements. Such materials include, but are not limited to: metal and semiconductor thin films, which may be fabricated through E-beam evaporation, thermal evaporation, sputter-coating, or other suitable techniques; conducting polymer thin films (e.g., poly-(3,4-ethylenedioxythiophene-polyaniline (PEDOT-PANI)) and composites of these, which may be deposited by direct ink writing, 3D printing, ink-jet printing, spin-coating, screen printing, tape casting, vapor phase deposition, in-situ polymerization, or other suitable techniques. Other materials that may be employed include composites and thin films based on embedded or self-assembled sheets of conducting particles (e.g., carbon nanotubes, carbon black (CB) particles, metal particles such as silver or gold particles, nanorods, nanowires, micro particles, conducting polymer particles), and liquid conductors (e.g., eutectic gallium-indium (eGaIn)), which may be deposited by direct ink writing, 3D printing, ink-jet printing, spin-coating, screen printing, tape casting, dip-pen lithography, spray coating, roll-to-roll lithography, Langmuir-deposition and stamping techniques; and conducting liquids, inks and gels.

Materials that may be used for the flexible substrate include, but are not limited to: low stiffness polymers and elastomers such as polydimethylsiloxane (PDMS), polyurethanes (PU), silicone-urethane copolymers, carbonate-urethane copolymers, polyisoprene, polybutadiene, copolymer of polystyrene and polybutadiene, chloroprene rubber, polyacrylic rubber (ACM, ABR), fluorosilicone rubber (FVMQ), fluoroelastomers, perfluoroelastomers, tetrafluoro ethylene/propylene rubbers (FEPM) and ethylene vinyl acetate (EVA), hydrogels such as gelatin, alginate, agarose, polyethylene glycol (PEG), polyacrylamide gels, poly(N-isopropylacrylamide), pHEMA, collagen, fibrin, and dextran, and porous and nanostructured scaffolds based on natural and synthetic polymers, such as, collagens, elastins, polysaccharides, and other extracellular matrix proteins, elastin-like peptides, polyhydroxyalkanoates, poly(glycerol-sebecate), polylactic acid, polyglycolic acid, and poly lactic glycolic acid copolymers. Examples of flexible supporting materials that may be used in the flexible substrate also appear in U.S. Pat. No. 8,492,150, Patent Application Publication No. US 2012/0142556 A1, and International Patent Application Publication No. WO 2013/086512 A2.

Sheets or scaffolds of aligned micron, submicron, or nanometer dimension polymeric fibers for use in the devices, constructs and methods of the invention comprise a plurality of fibers arrayed in substantially all the same direction (e.g., uniaxially aligned). In certain embodiments of the invention, the sheets or scaffolds of polymeric fibers may be mixtures of two or more polymers and/or two or more copolymers. In one embodiment the polymers may be a mixture of one or more polymers and or more copolymers. In another embodiment, the polymers for use in the devices and methods of the invention may be a mixture of one or more synthetic polymers and one or more naturally occurring polymers.

The terms "fiber" and "polymeric fiber" are used herein interchangeably, and both terms refer to fibers having micron, submicron, and nanometer dimensions.

Any suitable biogenic and/or non-biogenic polymer may be used to fabricate polymeric fiber sheets or scaffolds. Exemplary polymers for use in the devices, constructs, and methods of the invention may be biocompatible or nonbiocompatible, synthetic or natural and those such as those that are synthetically designed to have shear induced unfolding.

Suitable synthetic polymers include, for example, poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polyphosphazenes, polygermanes, polyorthoesters, polyesters, polyamides, polyolefins, polycarbonates, polyaramides, polyimides, copolymers and derivatives thereof, and combinations thereof.

Suitable biogenic polymers, include, for example, proteins, polysaccharides, lipids, nucleic acids or combinations thereof.

Exemplary biogenic polymers, e.g., fibrous proteins, for use in the devices, constructs and methods of the invention include, but are not limited to, extracellular matrix proteins, silk (e.g., fibroin, sericin, etc.), keratins (e.g., alpha-keratin which is the main protein component of hair, horns and nails, beta-keratin which is the main protein component of scales and claws, etc.), elastins (e.g., tropoelastin, etc.), fibrillin (e.g., fibrillin-1 which is the main component of microfibrils, fibrillin-2 which is a component in elastogenesis, fibrillin-3 which is found in the brain, fibrillin-4 which is a component in elastogenesis, etc.), fibrinogen/fibrins/thrombin (e.g., fibrinogen which is converted to fibrin by thrombin during wound healing), fibronectin, laminin, collagens (e.g., collagen I which is found in skin, tendons and bones, collagen II which is found in cartilage, collagen III which is found in connective tissue, collagen IV which is found in extracellular matrix (ECM) protein, collagen V which is found in hair, etc.), vimentin, neurofilaments (e.g., light chain neurofilaments NF-L, medium chain neurofilaments NF-M, heavy chain neurofilaments NF-H, etc.), amyloids (e.g., alpha-amyloid, beta-amyloid, etc.), actin, myosins (e.g., myosin I-XVII, etc.), titin which is the largest known protein (also known as connectin), etc.

Exemplary biogenic polymers, e.g., fibrous polysaccharides, for use in the devices, constructs, and methods of the invention include, but are not limited to, chitin which is a major component of arthropod exoskeletons, hyaluronic acid which is found in extracellular space and cartilage (e.g., D-glucuronic acid which is a component of hyaluronic acid, D-N-acetylglucosamine which is a component of hyaluronic acid, etc.), etc.

Exemplary glycosaminoglycans (GAGs)—carbohydrate polymers found in the body—for use in the devices, constructs, and methods of the invention include, but are not limited to, heparan sulfate founding extracelluar matrix, chondroitin sulfate which contributes to tendon and ligament strength, keratin sulfate which is found in extracellular matrix, etc.

In certain embodiments of the invention, a biologically active agent, e.g., a polypeptide, protein, nucleic acid molecule, nucleotide, lipid, biocide, antimicrobial, or pharmaceutically active agent, may be mixed with the polymer during the fabrication process of the polymeric fibers. In other embodiments, a biologically inert agent, e.g., fluorescent beads, e.g., fluorospheres, may be mixed with the polymer during the fabrication process.

In yet another embodiment, polymers for use in the polymeric fibers of the invention are naturally occurring polymers, e.g., biogenic polymers. Non-limiting examples of such naturally occurring polymers include, for example, polypeptides, proteins, e.g., capable of fibrillogenesis, polysaccharides, e.g., alginate, lipids, nucleic acid molecules, and combinations thereof.

The muscle tissue layer support by exemplary devices may be any of vascular smooth muscle cells, vascular endothelial cells, myocytes (e.g., cardiac myocytes), skeletal muscle, myofibroblasts, airway smooth muscle cells and cells that will differentiate into contractile cells (e.g., stem cells, e.g., embryonic stem cells or adult stem cells, progenitor cells or satellite cells).

These tissues may be based on human derived cells, e.g. induced pluripotent stem cells (IPS) or embryonic stem cells (ES), or from non-human animal sources including transgenic animals.

The term "progenitor cell" is used herein to refer to cells that have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "progenitor cell" is used herein synonymously with "stem cell."

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stemness." Self-renewal is the other classical part of the stem cell definition. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation".

The term "embryonic stem cell" is used to refer to the pluripotent stem cells of the inner cell mass of the embryonic blastocyst (see U.S. Pat. Nos. 5,843,780, 6,200,806, the contents of which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells.

In one embodiment, progenitor cells suitable for use in the claimed devices and methods are Committed Ventricular Progenitor (CVP) cells as described in PCT Application No. PCT/US09/060224, entitled "Tissue Engineered Myocardium and Methods of Productions and Uses Thereof", filed Sep. 28, 2009, the entire contents of which are incorporated herein by reference.

The tissue supporting layer includes molecules that support adhesion and ingrowth of seeded muscle tissues. Suitable molecules include, for example, extracellular matrix proteins (e.g., collagen, fibronectin, laminin, etc.); growth factors to direct cell function specific to cell type (e.g., nerve growth factor, bone morphogenic proteins, vascular endothelial growth factor, etc.); lipids, fatty acids and steroids (e.g., glycerides, non-glycerides, saturated and unsaturated fatty acids, cholesterol, corticosteroids, sex steroids, etc.); sugars and other biologically active carbohydrates (e.g., monosaccharides, oligosaccharides, sucrose, glucose, glycogen, etc.); combinations of carbohydrates, lipids and/or proteins, such as proteoglycans (protein cores with attached side chains of chondroitin sulfate, dermatan sulfate, heparin, heparan sulfate, and/or keratan sulfate); glycoproteins [e.g., selectins, immunoglobulins, hormones such as human chorionic gonadotropin, Alphafetoprotein and Erythropoietin (EPO), etc.]; proteolipids (e.g., N-myristoylated, palmitoylated and prenylated proteins); and glycolipids (e.g., glycoglycerolipids, glycosphingolipids, glycophosphatidylinositols, etc.); biologically derived homopolymers, such as polylactic and polyglycolic acids and poly-L-lysine; nucleic acids (e.g., DNA, RNA, etc.); hormones (e.g., anabolic steroids, sex hormones, insulin, angiotensin, etc.); enzymes (types: oxidoreductases, transferases, hydrolases, lyases, isomerases, ligases; examples: trypsin, collegenases, matrix metallproteinases, etc.); pharmaceuticals (e.g., beta blockers, vasodilators, vasoconstrictors, pain relievers, gene therapy, viral vectors, anti-inflammatories, etc.); cell surface ligands and receptors (e.g., integrins, selectins, cadherins, etc.); cytoskeletal filaments and/or motor proteins (e.g., intermediate filaments, microtubules, actin filaments, dynein, kinesin, myosin, etc.); and hydrophylic polymers (e.g., polyethylene oxide or pluronics).

Any appropriate cell culture method may be used to establish the tissue. The seeding density of the cells will vary depending on the cell size and cell type, but can easily be determined by methods known in the art. For example, the cells may be cultured in suitable media in an incubator under physiologic conditions (e.g., at 37° C.) until the cells form a tissue.

Figures 4A, 4B, 4C:
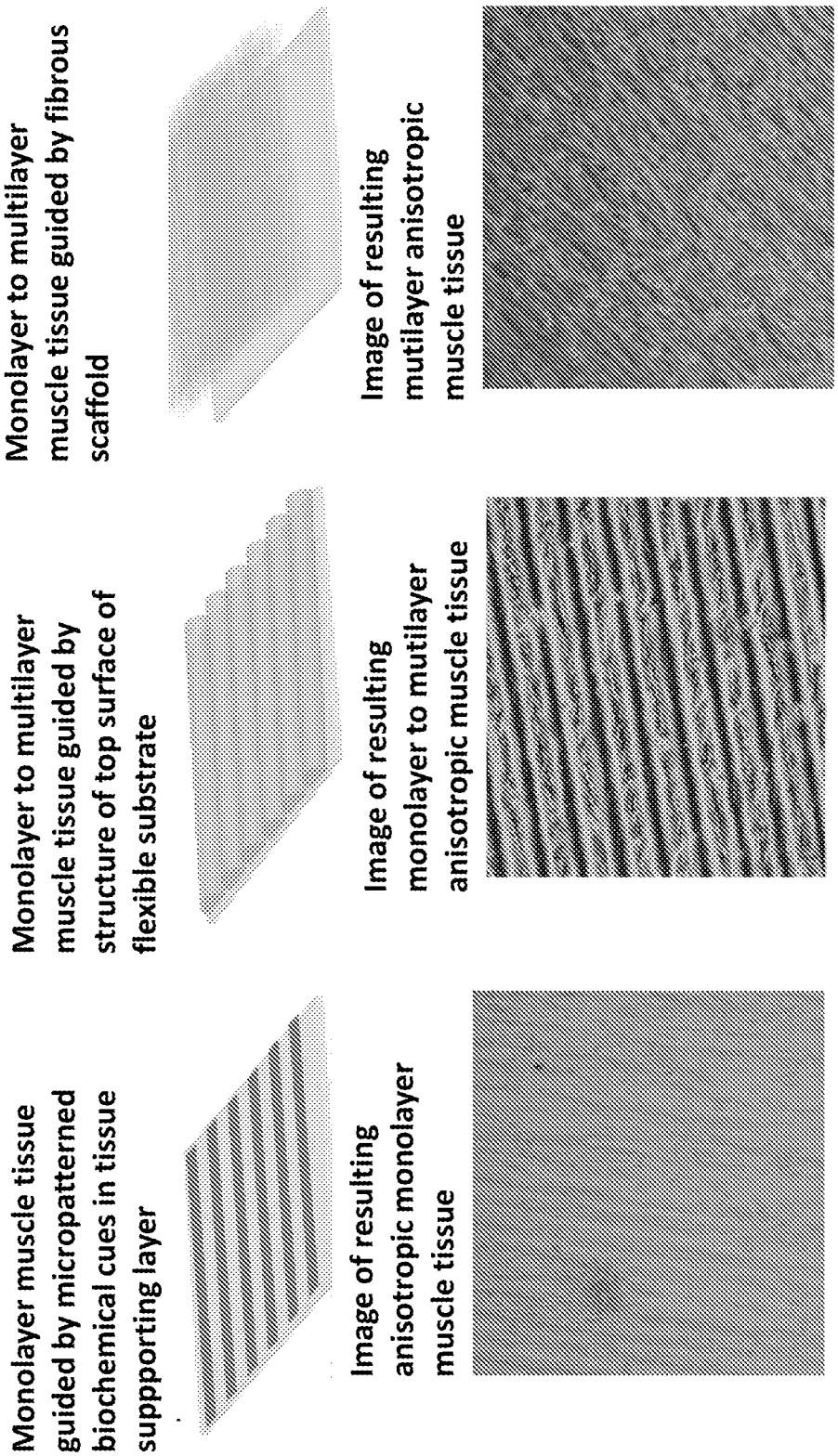
FIG. 4A schematically depicts employing micropatterned chemical cues (e.g., fibronectin or laminin proteins) on a tissue support layer to direct anisotropic muscle tissue growth and an image of the resulting neonatal rat cardiomyocyte (NRVM) tissue layer, in accordance with an embodiment.
FIG. 4B schematically depicts employing structural cues in a top surface of a flexible substrate to direct anisotropic muscle tissue growth and an image of the resulting neonatal rat cardiomyocyte (NRVM) tissue layer, in accordance with an embodiment.
FIG. 4C schematically depicts employing a fiber scaffold in the tissue support layer to direct anisotropic muscle tissue growth and an image of the resulting neonatal rat cardiomyocyte (NRVM) tissue layer, in accordance with an embodiment.

Anisotropic muscular tissues ranging from monolayer muscular thin films to multilayer 3-dimensional tissue, can be generated through (bio)-chemical, mechanical or structural cues or a combination of these as described below. FIGS. 4A-4C illustrate different options for directing development of anisotropic muscle tissue. In some embodiments, the tissue supporting layer includes chemical cues for development of anisotropic muscle tissue as shown in FIG. 4A. In such embodiments, the resulting tissue layer is typically only a single cell thick. Chemical cues that may be employed include, but are not limited to patterned proteins (e.g., fibronectin, collagen, or laminin), peptides or sugars to induce cellular binding and spreading, and polymers to limit spreading in defined areas using (e.g. pluronic, polyethylene glycol (PEG), poly(2-methyl-2-oxazoline) (PMOXA), and similar polymers). Patterning of such chemical cues can be achieved by a variety of different techniques, such as micro-contact printing, micromolding, screen and roll printing, direct ink printing, 3D printing, ink-jet printing, and UV induced patterning (e.g., stereo lithography). Example 1 described below describes a tissue support layer incorporating chemical cues for development of anisotropic muscle tissue.

In some embodiments, the tissue support layer itself incorporates a sheet of micron, submicron, and/or nanometer dimension fibers oriented in substantially the same direction forming a fiber scaffold to structurally direct anisotropic muscle tissue growth as shown in FIG. 4C. In such embodiments, the thickness of the muscle tissue layer depends on the thickness of the sheet of fibers. The muscle tissue layer could be a single cell thick or many cells thick. The muscle tissue layer can be between 10-100 microns thick, with the upper limit being set by diffusion of nutrients through the thickness of the muscle tissue layer. Fibrous sheets for cells scaffolds may be produced using multiple different techniques that include, but are not limited to: rotary jet spinning, electrospinning, immersed rotary jet spinning, and pull spinning. Because substantially all of the fibers are aligned in same direction, the ingrown tissue cells develop with a similar anisotropy. Sheets of fibers may be employed to produce both two dimensional (e.g., single cells thick layers) and three dimensional engineered tissue samples.

Example 2 below describes devices that incorporates a sheet of micron, submicron and/or nanometer dimension fibers to direct anisotropic muscle tissue growth. Additional details regarding formation of the fibers sheets are described below in the section entitled "Fiber Sheets for Tissue Supporting Layer." In other embodiments, the tissue supporting layer may include a cell scaffold of porous hydrogel or elastomer.

In some embodiments, the flexible substrate remains attached to and supported by a relatively rigid substrate during growth and development of the muscle layer. This is important because the cells require not only the spatial cues provided by the patterned chemical cues, structural cues, or fiber sheets, but also benefit from the relative inflexibility provided by the rigid substrate during culturing to prevent movement of the cells during growth and development in order to form a functional tissue. In the absence of these restrictions, the cells may not organize relative to the cues provided by the patterned chemical cues, structural cues, or fiber sheets and may not be held in place for a sufficient period of time in order for the cells to properly organize, differentiate, and mature into functional two-dimensional tissue as they would in an in vivo environment. Further, if there is prestress in the flexible substrate, the flexible substrate may need to remain attached to the rigid substrate during development of the muscle tissue. In some embodiments, attachment to the underlying rigid substrate may not be needed for development of the muscle tissue layer and the flexible substrate may be released from the underlying rigid substrate prior to growth and development of the tissue layer.

In some embodiments, a top surface of the flexible substrate has a shape that structurally directs anisotropic muscle tissue growth as shown in FIG. 4B. Structural cues can be generated in a top surface of the flexible substrate, which may comprise a hydrogel or an elastomer, by additive or subtractive techniques. Such techniques include, but are not limited to, imprint and molding techniques, photolithographic techniques, lithographically directed etching, UV-induced crosslinking polymerization or vapor polymerization, spray coating deposition, screen and roll-to-roll deposition, laser cutting and crosslinking techniques, direct-ink printing, 3D-printing and ink jet printing. In some embodiments, mechanical cues can be achieved by locally patterned stiffness, in addition to, or as opposed to locally patterned shape. Such patterned stiffness may be achieved through differences in crosslinking of degree of elastomeric substrates, or localized differences in solid content of a hydrogel material.

Fiber Sheets for Tissue Supporting Layer

In some embodiments, suitable devices for fabricating the micron, submicron or nanometer dimension polymeric fibers include a reservoir for holding a polymer, the reservoir including one or more orifices for ejecting the polymer during fiber formation, thereby forming a micron, submicron or nanometer dimension polymeric fiber and a collection device for accepting the formed micron, submicron or nanometer dimension polymeric fiber, wherein at least one of the reservoir and the collection device employs rotational motion during fiber formation, and the device is free of an electrical field, e.g., a high voltage electrical field.

The device may include a rotary motion generator for imparting a rotational motion to the reservoir and, in some exemplary embodiments, to the collection device. In some embodiments, a flexible air foil is attached to a shaft of the motor above the reservoir to facilitate fiber collection and solvent evaporation.

Rotational speeds of the reservoir in exemplary embodiments may range from about 1,000 rpm-60,000 rpm, about 1,000 rpm-50,000 rpm, about 1,000 rpm to about 40,000 rpm, about 1,000 rpm-30,000 rpm, about 1,000 rpm to about 20,000 rpm, about 1,000 rpm-10,000 rpm, about 5,000 rpm-60,000 rpm, about 5,000 rpm-50,000 rpm, about 5,000 rpm to about 40,000 rpm, about 5,000 rpm-30,000 rpm, about 5,000 rpm-20,000 rpm, about 5,000 rpm to about 15,000 rpm, about 5,000 rpm-10,000 rpm, about 10,000 rpm-60,000 rpm, about 10,000 rpm-50,000 rpm, about 10,000 rpm to about 40,000 rpm, about 10,000 rpm-30,000 rpm, about 10,000 rpm-20,000 rpm, about 10,000 rpm to about 15,000 rpm, about 20,000 rpm-60,000 rpm, about 20,000 rpm-50,000 rpm, about 20,000 rpm to about 40,000 rpm, about 20,000 rpm-30,000 rpm, or about 50,000 rpm to about 400,000 rpm, e.g., about 1,000, 1,500, 2,000, 2,500, 3,000, 3,500, 4,000, 4,500, 5,000, 5,500, 6,000, 6,500, 7,000, 7,500, 8,000, 8,500, 9,000, 9,500,10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 55,000, 60,000, 65,000, 70,000, 75,000, 80,000, 85,000, 90,000, 95,000, 100,000, 105,000, 110,000, 115,000, 120,000, 125,000, 130,000, 135,000, 140,000, 145,000, 150,000 rpm, about 200,000 rpm, 250,000 rpm, 300,000 rpm, 350,000 rpm, or 400,000 rpm. Ranges and values intermediate to the above recited ranges and values are also contemplated to be part of the invention.

In certain embodiments, rotating speeds of about 50,000 rpm-400,000 rpm are intended to be encompassed by the methods of the invention. In one embodiment, devices employing rotational motion may be rotated at a speed greater than about 50,000 rpm, greater than about 55,000 rpm, greater than about 60,000 rpm, greater than about 65,000 rpm, greater than about 70,000 rpm, greater than about 75,000 rpm, greater than about 80,000 rpm, greater than about 85,000 rpm, greater than about 90,000 rpm, greater than about 95,000 rpm, greater than about 100,000 rpm, greater than about 105,000 rpm, greater than about 110,000 rpm, greater than about 115,000 rpm, greater than about 120,000 rpm, greater than about 125,000 rpm, greater than about 130,000 rpm, greater than about 135,000 rpm, greater than about 140,000 rpm, greater than about 145,000 rpm, greater than about 150,000 rpm, greater than about 160,000 rpm, greater than about 165,000 rpm, greater than about 170,000 rpm, greater than about 175,000 rpm, greater than about 180,000 rpm, greater than about 185,000 rpm, greater than about 190,000 rpm, greater than about 195,000 rpm, greater than about 200,000 rpm, greater than about 250,000 rpm, greater than about 300,000 rpm, greater than about 350,000 rpm, or greater than about 400,000 rpm.

Exemplary devices employing rotational motion may be rotated for a time sufficient to form a desired polymeric fiber, such as, for example, about 1 minute to about 100 minutes, about 1 minute to about 60 minutes, about 10 minutes to about 60 minutes, about 30 minutes to about 60 minutes, about 1 minute to about 30 minutes, about 20 minutes to about 50 minutes, about 5 minutes to about 20 minutes, about 5 minutes to about 30 minutes, or about 15 minutes to about 30 minutes, about 5-100 minutes, about 10-100 minutes, about 20-100 minutes, about 30-100 minutes, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 minutes, or more. Times and ranges intermediate to the above-recited values are also intended to be part of this invention.

In some embodiments, the reservoir may not be rotated, but may be pressurized to eject the polymer material from the reservoir through one or more orifices. For example, a mechanical pressurizer may be applied to one or more surfaces of the reservoir to decrease the volume of the reservoir, and thereby eject the material from the reservoir. In another exemplary embodiment, a fluid pressure may be introduced into the reservoir to pressurize the internal volume of the reservoir, and thereby eject the material from the reservoir. An exemplary reservoir may have a volume ranging from about one nanoliter to about 1 milliliter, about one nanoliter to about 5 milliliters, about 1 nanoliter to about 100 milliliters, or about one microliter to about 100 milliliters, for holding the liquid material. Some exemplary volumes include, but are not limited to, about one nanoliter to about 1 milliliter, about one nanoliter to about 5 milliliters, about 1 nanoliter to about 100 milliliters, one microliter to about 100 microliters, about 1 milliliter to about 20 milliliters, about 20 milliliters to about 40 milliliters, about 40 milliliters to about 60 milliliters, about 60 milliliters to about 80 milliliters, about 80 milliliters to about 100 milliliters, but are not limited to these exemplary ranges. Exemplary volumes intermediate to the recited volumes are also part of the invention. In certain embodiment, the volume of the reservoir is less than about 5, less than about 4, less than about 3, less than about 2, or less than about 1 milliliter. In other embodiments, the physical size of an unfolded polymer and the desired number of polymers that will form a fiber dictate the smallest volume of the reservoir.

In one embodiment, a polymer is fed into a reservoir as a polymer solution, i.e., a polymer dissolved in an appropriate solution. In this embodiment, the methods may further comprise dissolving the polymer in a solvent prior to feeding the polymer into the reservoir. In other embodiments, a polymer is fed into the reservoir as a polymer melt. In such embodiment, the reservoir is heated at a temperature suitable for melting the polymer, e.g., is heated at a temperature of about 100° C. to about 300° C., 100-200° C., about 150-300° C., about 150-250° C., or about 150-200° C., or about 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or about 300° C.

The reservoir includes one or more orifices through which one or more jets of the material solution (e.g., polymer solution) are forced to exit the reservoir by the motion of the reservoir during fiber formation. One or more exemplary orifices may be provided on any suitable side or surface of the reservoir including, but not limited to, a bottom surface of the reservoir that faces the collection device, a side surface of the reservoir, a top surface of the reservoir that faces in the opposite direction to the collection device, etc. Exemplary orifices may have any suitable cross-sectional geometry including, but not limited to, circular, oval, square, rectangular, etc. In an exemplary embodiment, one or more nozzles may be provided associated with an exemplary orifice to provide control over one or more characteristics of the material solution exiting the reservoir through the orifice including, but not limited to, the flow rate, speed, direction, mass, shape and/or pressure of the material solution. The locations, cross-sectional geometries and arrangements of the orifices on the reservoir, and/or the locations, cross-sectional geometries and arrangements of the nozzles on the orifices, may be configured based on the desired characteristics of the resulting fibers and/or based on one or more other factors including, but not limited to, viscosity of the material solution, the rate of solvent evaporation during fiber formation, etc.

Exemplary orifice lengths that may be used in some exemplary embodiments range between about 0.001 m and about 0.05 m, e.g., 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, or 0.05. In some embodiments, exemplary orifice lengths that may be used range between about 0.002 m and 0.01 m. Ranges and values intermediate to the above recited ranges and values are also contemplated to be part of the invention.

Exemplary orifice diameters that may be used in some exemplary embodiments range between about 0.1 µm and about 10 µm, about 50 µm to about 500 µm, about 200 µm to about 600 µm, about 200 µm to about 1,000 µm, about 500 µm to about 1,000 µm, about 200 µm to about 1,500 µm, about 200 µm to about 2,000 µm, about 500 µm to about 1,500 µm, or about 500 µm to about 2,000 µm, e.g., about 10, 20, 30, 40, 50, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, or about 2,000 µm. Ranges and values intermediate to the above recited ranges and values are also contemplated to be part of the invention.

In other embodiments, a suitable device for the formation of a micron, submicron or nanometer dimension polymeric fibers includes a reservoir for holding a polymer, the reservoir including one or more orifices for ejecting the polymer during fiber formation, thereby forming micron, submicron or nanometer dimension polymeric fibers, a collection device and an air vessel for circulating a vortex of air around the formed fibers to wind the fibers into one or more threads.

In yet other embodiments, a suitable device for the formation of a micron, submicron or nanometer dimension polymeric fiber includes a reservoir for holding a polymer, the reservoir including one or more orifices for ejecting the polymer during fiber formation, thereby forming a micron, submicron or nanometer dimension polymeric fiber, a collection device, one or more mechanical members disposed or formed on or in the vicinity of the reservoir for increasing an air flow or an air turbulence experienced by the polymer ejected from the reservoir, and a collection device for accepting the formed micron, submicron or nanometer dimension polymeric fiber.

In some embodiments, a suitable device for the formation of a micron, submicron or nanometer dimension polymeric fiber includes a reservoir holding a polymer solution. The reservoir includes a surface having one or more orifices for ejecting the polymer solution from the reservoir for fiber formation. The device also includes a motion generator configured to impart rotational motion to the reservoir so that the rotational motion causes ejection of the polymer solution from the reservoir through the one or more orifices. The device also includes a collection device holding a liquid and configured and positioned to accept the polymer solution ejected from the reservoir. The reservoir and the collection device are positioned such that the one or more orifices of the reservoir are submerged in the liquid in the collection device. The ejection of the polymer solution into the liquid in the collection device causes formation of one or more micron, submicron or nanometer dimension polymeric fibers.

In yet other embodiments, a suitable device for the formation of a micron, submicron or nanometer dimension polymeric fiber includes a reservoir for holding a polymer and including an outer surface having one or more orifices for ejecting the polymer for fiber formation. The device may further include a first motion generator coupleable to the reservoir, the first motion generator configured to impart rotational motion to the reservoir to cause ejection of the polymer through the one or more orifices. The device may further include a collection device holding a liquid, the collection device configured and positioned to accept the polymer ejected from the reservoir, a second motion generator coupleable to the collection device, the second motion generator configured to impart rotational motion to the liquid in the collection device to generate a liquid vortex including an air gap, wherein the reservoir and the collection device are positioned such that the one or more orifices of the reservoir are positioned in the air gap of the liquid vortex in the collection device; and wherein the ejection of the polymer into the air gap and subsequently into the liquid of the liquid vortex in the collection device causes formation of one or more micron, submicron or nanometer dimension polymeric fibers.

The air gap may be positioned centrally in the liquid vortex in the collection device.

The first and second motion generators may impart rotational motion in the same or opposite rotational direction.

In one embodiment, a suitable device further comprises a component suitable for continuously feeding the polymer into the rotating reservoir (or a platform), such as a spout or syringe pump.

An exemplary method to fabricate the micron, submicron or nanometer dimension polymeric fibers may include imparting rotational motion to a reservoir holding a polymer, the rotational motion causing the polymer to be ejected from one or more orifices in the reservoir and collecting the formed fibers to form the micron, submicron or nanometer dimension polymeric fibers.

In one embodiment, the methods include feeding a polymer into a rotating reservoir of a device of the invention and providing motion at a speed and for a time sufficient to form a micron, submicron or nanometer dimension polymeric fiber, and collecting the formed fibers to form the micron, submicron or nanometer dimension polymeric fibers.

In another embodiment, the methods include providing a polymer solution and imparting a sufficient amount of shear stress to the polymer solution for a time sufficient to form a micron, submicron or nanometer dimension polymeric fiber, and collecting the formed fibers to form the micron, submicron or nanometer dimension polymeric fibers. In one embodiment, a sufficient amount of shear stress in about 3,000 Pascals.

In another embodiment, the methods include feeding a polymer solution into a rotating reservoir of a device of the invention and providing an amount of shear stress to the rotating polymer solution for a time sufficient to form a micron, submicron or nanometer dimension polymeric fiber, and collecting the formed fibers to form the micron, submicron or nanometer dimension polymeric fibers.

Another exemplary method to fabricate the micron, submicron or nanometer dimension polymeric fibers includes providing a polymer in solution, rotating the polymer in solution about an axis of rotation to cause ejection of the polymer solution in one or more jets, generating a liquid vortex in a collection device for collecting the one or more jets of the polymer, the liquid vortex including a central air gap, and collecting the one or more jets of the polymer in the collection device, wherein the one or more jets are initially ejected through the air gap of the liquid vortex and subsequently through the liquid in the liquid vortex of the collection device, wherein the ejection of the polymer into the air gap and subsequently into the liquid in the collection device causes formation of one or more micron, submicron or nanometer dimension polymeric fibers.

In other embodiments of the inventions, suitable devices for fabricating the micron, submicron or nanometer dimension polymeric fibers include a platform for supporting a stationary deposit of a polymer, a rotating structure disposed vertically above the platform and spaced from the platform along a vertical axis, and a collection device. The rotating structure includes a central core rotatable about a rotational axis, and one or more blades affixed to the rotating core. The rotating structure is configured and operable so that, upon rotation, the one or more blades contact a surface of the polymer to impart sufficient force in order to decouple a portion of the polymer from contact with the one or more blades of the rotating structure and to fling the portion of the polymer away from the contact with the one or more blades and from the deposit of the polymer, thereby forming a micron, submicron and/or nanometer dimension polymeric fiber.

Sufficient rotational speeds and times for operating the rotating structure to form a fiber may be dependent on the concentration of the material and the desired features of the formed fiber. Exemplary speeds of rotation of the rotating structure may range from about 100 rpm to about 500,000 rpm, although rotational speeds are not limited to this exemplary range. Certain exemplary devices employing rotational motion may be rotated at a speed of about 1,000 rpm-60,000 rpm, about 1,000 rpm-50,000 rpm, about 1,000 rpm to about 40,000 rpm, about 1,000 rpm-30,000 rpm, about 1,000 rpm to about 20,000 rpm, about 1,000 rpm-10,000 rpm, about 5,000 rpm-60,000 rpm, about 5,000 rpm-50,000 rpm, about 5,000 rpm to about 40,000 rpm, about 5,000 rpm-30,000 rpm, about 5,000 rpm-20,000 rpm, about 5,000 rpm to about 15,000 rpm, about 5,000 rpm-10,000 rpm, about 10,000 rpm-60,000 rpm, about 10,000 rpm-50,000 rpm, about 10,000 rpm to about 40,000 rpm, about 10,000 rpm-30,000 rpm, about 10,000 rpm-20,000 rpm, about 10,000 rpm to about 15,000 rpm, about 20,000 rpm-60,000 rpm, about 20,000 rpm-50,000 rpm, about 20,000 rpm to about 40,000 rpm, about 20,000 rpm-30,000 rpm, or about 50,000 rpm to about 400,000 rpm, e.g., about 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 55,000, 60,000, 65,000, 70,000, 75,000, 80,000, 85,000, 90,000, 95,000, 100,000, 105,000, 110,000, 115,000, 120,000, 125,000, 130,000, 135,000, 140,000, 145,000, 150,000 rpm, about 200,000 rpm, 250,000 rpm, 300,000 rpm, 350,000 rpm, or 400,000 rpm. Ranges and values intermediate to the above recited ranges and values are also contemplated to be part of the invention. For example, rotating speeds of about 10,000 rpm-15,000 rpm, or 8,000 rpm-12,000 rpm are intended to be encompassed by the methods of the invention.

In one embodiment, devices employing rotational motion may be rotated at a speed greater than about 1,000 rpm, greater than about 1,500 rpm, greater than about 2,000 rpm, greater than about 2,500 rpm, greater than about 3,000 rpm, greater than about 3,050 rpm, greater than about 3,100 rpm, greater than about 3,150 rpm, greater than about 3,200 rpm, greater than about 3,250 rpm, greater than about 3,300 rpm, greater than about 3,350 rpm, greater than about 3,400 rpm, greater than about 3,450 rpm, greater than about 3,500 rpm, greater than about 3,550 rpm, greater than about 3,600 rpm, greater than about 3,650 rpm, greater than about 3,700 rpm, greater than about 3,750 rpm, greater than about 3,800 rpm, greater than about 3,850 rpm, greater than about 3,900 rpm, greater than about 3,950 rpm, or greater than about 4,000 rpm. Speeds intermediate to the above recited speeds are also contemplated to be part of the invention.

An exemplary rotating structure may be rotated to impact the liquid material for a time sufficient to form a desired fiber, such as, for example, about 1 minute to about 100 minutes, about 1 minute to about 60 minutes, about 10 minutes to about 60 minutes, about 30 minutes to about 60 minutes, about 1 minute to about 30 minutes, about 20 minutes to about 50 minutes, about 5 minutes to about 20 minutes, about 5 minutes to about 30 minutes, or about 15 minutes to about 30 minutes, about 5-100 minutes, about 10-100 minutes, about 20-100 minutes, about 30-100 minutes, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 minutes, or more. Times and ranges intermediate to the above-recited values are also intended to be part of this invention.

The one or more portions or components of the rotating structure may penetrate into the surface of the liquid material to a desired depth. Exemplary depths of penetration may range from about one nanometer to about one centimeter, but are not limited to this range. Some exemplary penetration depths include, but are not limited to, about one millimeter to about twenty milliliters, about twenty milliliters to about forty milliliters, about forty milliliters to about sixty milliliters, about sixty milliliters to about eighty milliliters, about eighty milliliters to about one hundred milliliters, about one centimeter, and the like. Exemplary penetration depths intermediate to the above-recited exemplary values are also intended to be part of this invention.

The rotating structure may be configured in any suitable manner so that, upon rotation, the rotating structure contacts a surface of the liquid material on platform to impart sufficient force or energy to create a meniscus at the location where the rotating structure contacts the surface. The force or energy imparted by the rotating structure overcomes the surface tension and decouples a portion of the liquid material at the meniscus and flings the portion away from the contact with the rotating structure and from the platform, thereby forming a micron, submicron and/or nanometer dimension fiber. The fiber may be collected on the collection device. In an exemplary embodiment, the direction in which the liquid material is flung may be substantially the same as the tangential direction of motion of the component of the rotating structure that contacts the liquid material. In an exemplary embodiment, the rotating structure may impart a force to the liquid material in a substantially parallel direction to the top surface of the liquid material.

In one embodiment, the rotating structure may have a central core rotatable in a clockwise and/or counter-clockwise manner about a central axis of rotation R. In an exemplary embodiment, the rotational axis R may be offset at substantially 90 degrees from the vertical axis V. The core may have a substantially cylindrical shape with a substantially circular cross-section having a center aligned along the axis of rotation R. The rotating structure may also include one or more protrusions, e.g., in the form of blades, brushes, bristles, etc., affixed to the outer surface of the rotating core so that part of the protrusions penetrate into the surface of the liquid material. Exemplary rotating structures may include any suitable number of protrusions affixed to the core including, but not limited to, one protrusion to 500 protrusions. Some exemplary numbers of protrusions include, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 50 to about 100, about 100 to about 200, about 200 to about 300, about 300 to about 400, about 400 to about 500, and the like. Exemplary numbers of protrusions intermediate to the recited exemplary numbers are also part of the invention. The protrusions may be configured on the core in any suitable arrangement including, but not limited to, a regular multi-row or multi-column arrangement, an array pattern, a circular arrangement, a random arrangement, and the like.

Each protrusion may have any suitable shape including, but not limited to, a substantially rectangular shaped protrusion, a saw shaped protrusion wherein the base of the protrusion at the core is wider than the tip farthest from the core, a cylindrical shaped protrusion, and the like. At high rotational speeds and/or in instances where broken protrusions would compromise the purity of the fibers, the saw shape may provide enhanced structural integrity to the protrusions and may prevent break-off of the protrusions during rotation.

In some exemplary embodiments, one or more aspects of the protrusions on the rotating structure may be varied to control the adherence of the liquid material to the protrusions when the liquid material comes into contact with the protrusions, thereby facilitating fiber formation. Exemplary aspects that may be control or configured include, but are not limited to, the surface chemistry of the protrusions, the surface topography of the protrusions (e.g., a rougher texture), a geometry of the protrusions (e.g., a cross-sectional shape of the protrusions), and the like. In addition, configuring these aspects of the protrusions may allow controlling the geometry of the fibers that are formed, fiber width, surface features on the fibers, and the like.

Exemplary protrusions may be formed of any suitable material including, but not limited to, titanium, stainless steel (e.g., 300 and 400 alloys), aluminum (e.g., 6061, 7075), polystyrene, polypropylene, (e.g., UHMW, HDPE, LDPE), ABS, acetal (copolymer and homopolymer), nylon, polycarbonate, polyether ether ketone, polymethyl methacrylate, polysulfone, polytetrafluoroethylene, polyvinylchloride, and the like.

Any suitable size or geometrically shaped reservoir or collector may be used for fabricating polymeric fibers.

In some embodiments, the fibers may be produced by electrospinning or other suitable techniques known to those in the art.

Figure 5:
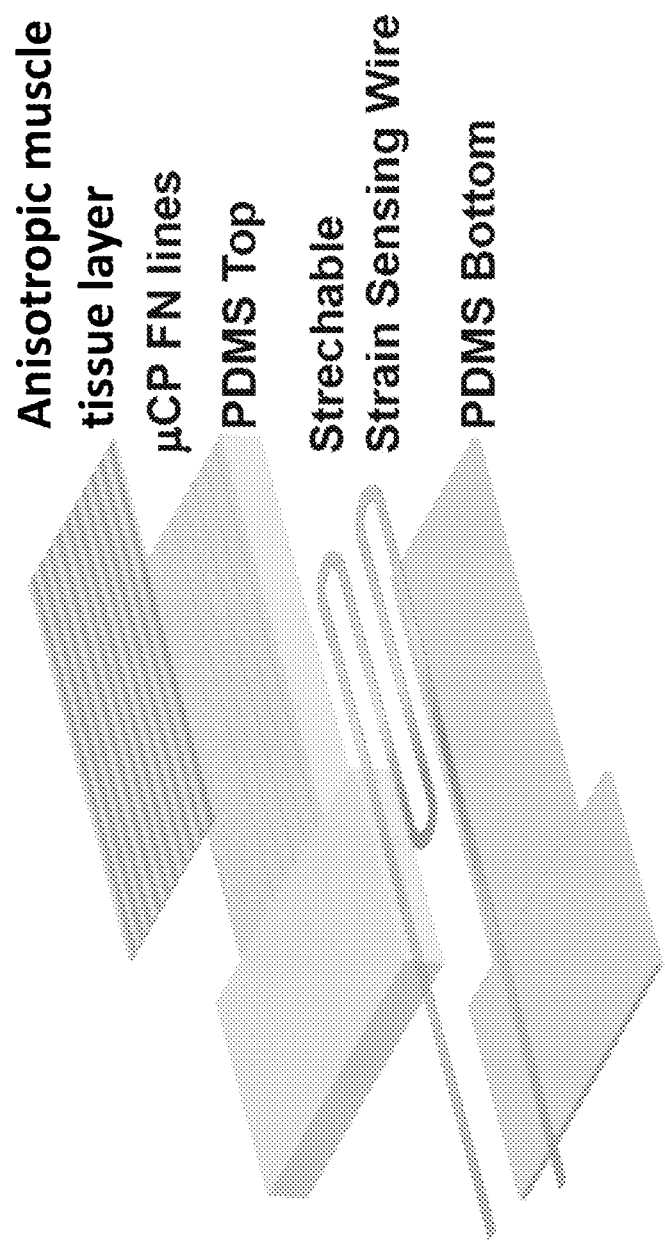
FIG. 5 schematically depicts an exploded perspective view of an example cantilever geometry device employing piezoresistive strain sensing and chemical cues to direct growth of anisotropic muscle tissue.

Example 1—Muscular Tissue Piezoresistive Strain Gauge Device with Micropatterned Chemical Cues and Multiplexed Apparatus A cantilever geometry device for measuring a contractile function of a muscle tissue layer that employed a pieozoresistive stretchable metal nanofilm wire embedded in a polymer flexible substrate, specifically polydimethylsiloxane (PDMS), was produced. The tissue supporting layer of the device employed micropatterned chemical cues, specifically micro-contact printed (µCP) fibronectin (FN), for promoting anisotropic growth of the muscle tissue layer. The strain-sensitive element employed was a stretchable piezoresistive micro-cracked gold thin film. FIG. 5 schematically depicts an exploded perspective view of the device.

Figure 6A:
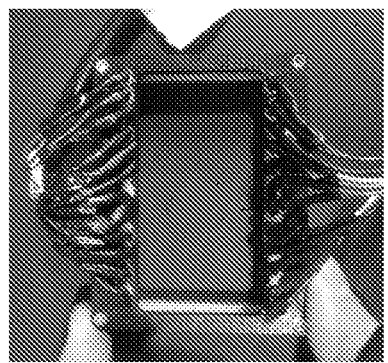
FIG. 6A is an image of a multiplexed apparatus incorporating eight devices of the design depicted in FIG. 5 each including an integrated half Wheatstone bridge for measuring a change in resistance as a change in voltage in accordance with some embodiments.
Figure 6B:
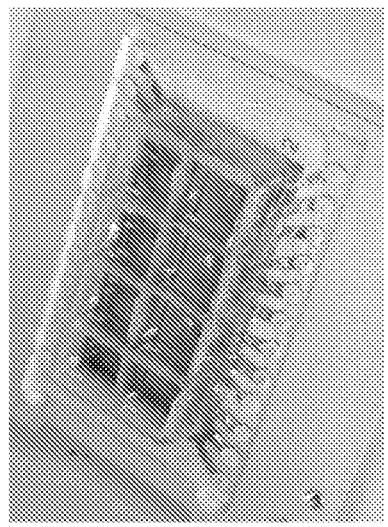
FIG. 6B is an image of the multiplexed apparatus of FIG. 6A after addition of a plurality of wells with each well associated with a corresponding independent device, in accordance with some embodiments.
Figure 6C:
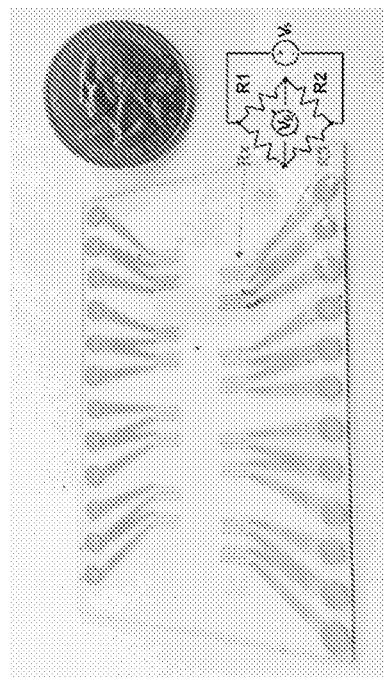
FIG. 6C is an image of a holder for the multiplexed apparatus of FIG. 6B incorporating electrical contacts to leads for each independent device, in accordance with some embodiments.

An eight-well apparatus was also produced based on this device design, with each well including an independent device and an associated half Wheatstone bridge enabling resistance changes to be recorded as voltage changes. FIG. 6A shows the multiplexed apparatus incorporating eight independent devices each including an integrated half Wheatstone bridge for measuring a change in resistance as a change in voltage. FIG. 6B is an image of the multiplexed apparatus after addition of eight wells with each well associated with a corresponding independent device. FIG. 6C shows the multiplexed apparatus in a holder incorporating electrical contacts to leads for each independent device. The holder was used for recording from the eight-well apparatus inside an incubator.

Fabrication

A 2"×3" glass slide served as a rigid substrate for formation of the devices. Poly(N-isopropylacrylamide) (pnipaam) thin film islands served as a sacrificial release layer between the rigid substrate and the flexible substrate. The pnipaam thin film islands were made by spin coating or printing pnipaam solution in 1-butanol or iso-priponal onto the rigid substrate. Alternatively, other water-soluble polymers such as dextran or sucrose could have been employed for the sacrificial layer (also referred to herein as the release layer). A first polymer substrate layer in the form of a 3-4 μm thick SYLGARD 184 PDMS film was spin coated onto the rigid substrate over the release layer. (SYLGARD is a registered trademark of Dow Corning Corporation.)

Thermal or e-beam evaporated titanium-gold or chromium-gold thin films on PDMS substrates spontaneously develop micro-wrinkled or micro-cracked films. The specific microstructure can be controlled through the thickness of the Ti or Cr adhesion layer. A thin film of Ti—Au—Ti was evaporated onto the first polymer layer with nominal thicknesses 3 nm Ti, 20 nm Au, 1 nm Ti, using a custom-made shadow mask to define a wire pattern for each device. After evaporation, prestresses in the metal wires were released by heat-treatment at 190 C for 30-50 min.

Figure 7:
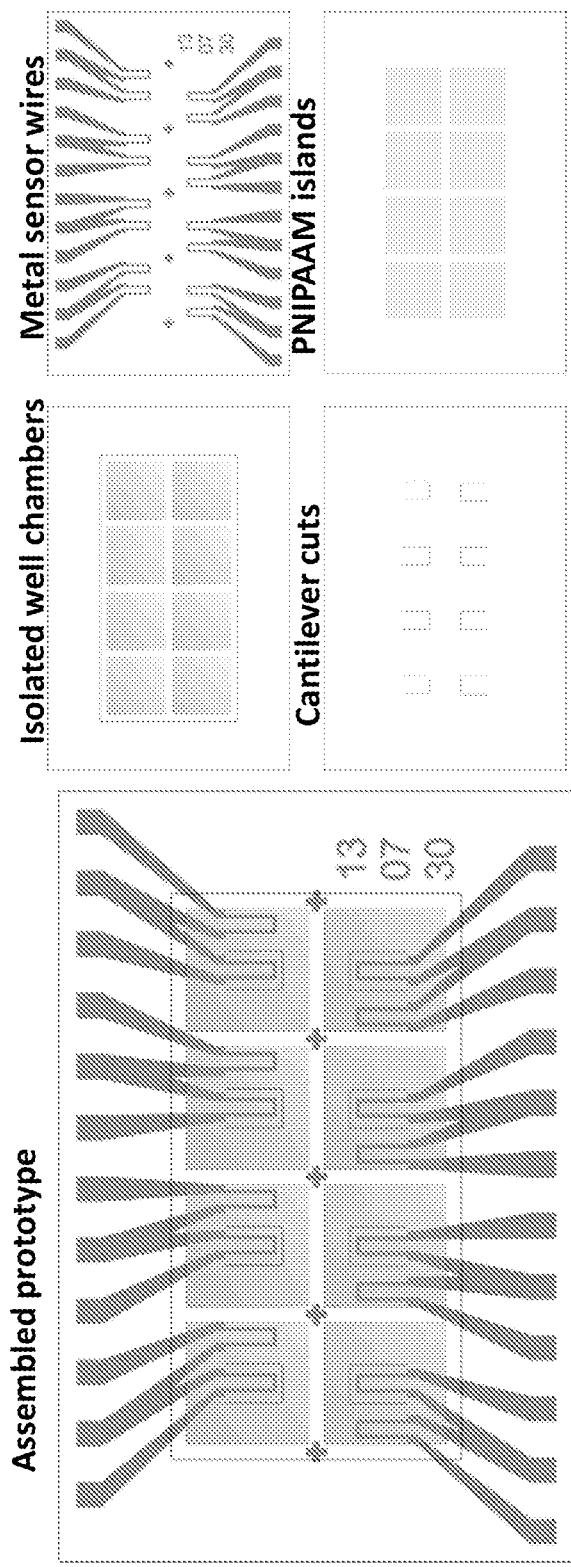
FIG. 7 schematically illustrates the design and various steps in processing of the eight well multiplexed apparatus of FIG. 6A, in accordance with some embodiments.

A second polymer substrate layer in the form of a 25 um PDMS film was spin coated on the substrate over the wires and over the first polymer substrate layer. After curing, separate cantilevers were cut in the PDMS using a $CO_2$ laser. The PDMS polymer substrate layers had an elastic modulus of about 1.5 MPa. A tissue supporting layer was formed on each device in the form of a pattern of 15 μm wide lines of fibronectin spaced by 2-4 μm for each device, which was transferred to the substrate using micro-contact printing. FIG. 6A shows the eight devices. Laser cut plastics or cast PDMS wells were used to contain cell medium (see FIG. 6B). FIG. 7 schematically illustrates the patterns used for various steps for the design of the eight well apparatus. Laser cuts in the PDMS and a PNIPAAM release layer below the sensor enabled for the fabrication of cantilevers. The wire layout facilitates Wheatstone bridge measurements of the resistance change, and concurrent control for temperature changes.

After placement of the wells, neonatal rat ventricular myocytes (NRVM) were seeded at a concentration of 0.3 Mio cells per ml medium, and the contraction of the resulting muscle tissue layers was tested on day 4-5 after seeding. Prior to testing, the cantilevers were released by lowering the sample temperature to room temperature to dissolve the pnipaam sacrificial layer, meaning that the flexible substrate cantilevers were released from the underlying rigid glass substrate after development and growth of the tissue.

The custom holder shown in FIG. 6C allowed in-line in incubator studies of tissue contraction.

Figure 8:
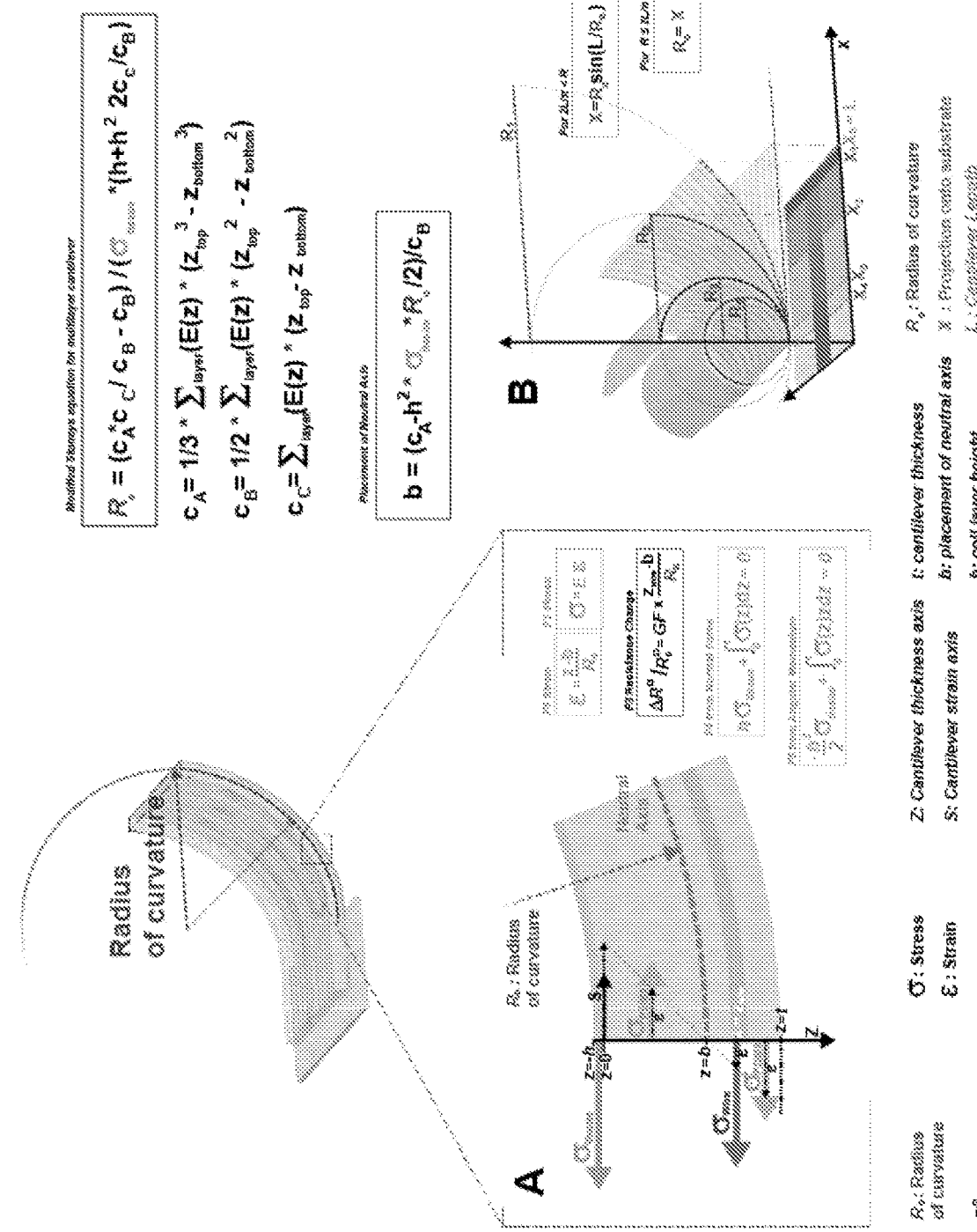
FIG. 8 schematically illustrates parameters and equations for calculating stress in the muscle tissue film from a change in resistance of the piezoresistive wire for the device of FIG. 5.

Stress in the overlying muscle tissue layer due to contraction can be determined from measured changes in resistance in the piezoelectric wire. FIG. 8 schematically depicts the various parameters used for relating the change in resistance to change in the stress in the muscle tissue layer. The following equations can be used to relate change in resistance of the wire to stress in the muscle tissue film using the parameters.

The strain is described by the following equation F1.

$$\varepsilon(z) = \frac{z - b}{R_c}$$

The stress is related to the strain by the following equation F2.

$$\sigma = E\varepsilon$$

The resistance change in the wire is described by the following equation F3.

$$\Delta R^\Omega / R_0^\Omega = GF \times \frac{z_{wire} - b}{R_c}$$

The following equation F4 describes the normal force in the muscle tissue layer being balanced by the total normal force throughout the flexible substrate.

$$h\sigma_{tissue} + \int_0^s \sigma(z)dz = 0$$

The following equation F5 describes the angular momentum in the muscle tissue layer being balanced by the total angular momentum throughout the flexible substrate.

$$\frac{-h^2}{2}\sigma_{tissue} + \int_0^t \sigma(z)z\,dz = 0$$

In the equations above, $\varepsilon(z)$ is the strain at a distance (z) from the surface of the flexible substrate, $\sigma$ is the stress, E is the elastic modulus, b is the z value of the neutral axis (i.e., where the beam is not under compressive or tensile stress), $z_{wire}$ is the z value at the wire, $R_c$ is the radius of curvature at the neutral axis, GF is the gauge factor of the wire, h is the thickness of the tissue, t is the thickness of the flexible substrate, $R_0^\Omega$ is the unstrained resistance, and $\Delta R^\Omega$ is the change in resistance.

The following modified Stoney's equation may be employed for calculating the radius of curvature:

$$R_0 = \left(\frac{c_A * c_C}{c_B} - c_B\right) \Big/ \left(\sigma_{tissue} * \left(h + h^2 2\frac{c_C}{c_B}\right)\right)$$

where $$c_A = \frac{1}{3} * \sum_{layer} (E(z) * (z_{top}^3 - z_{bottom}^3))$$

$$c_B = \frac{1}{2} * \sum_{layer} (E(z) * (z_{top}^2 - z_{bottom}^2))$$

$$c_C = \frac{1}{2} * \sum_{layer} (E(z) * (z_{top} - z_{bottom}))$$

and the placement of the neutral axis is given by $$b = \frac{\left(c_A - h^2 * \sigma_{tissue} * \frac{R_0}{2}\right)}{c_B}$$

For this design, the further the distance between the neutral axis and the wire (i.e., the larger the value of $z_{wire}$-b) the larger the strain signal. Thus, for a given total thickness of the flexible substrate, the smaller the thickness of the first polymer substrate layer, the greater the strain signal.

Development of Ti—Au—Ti Piezoelectric Wires

Figure 9:
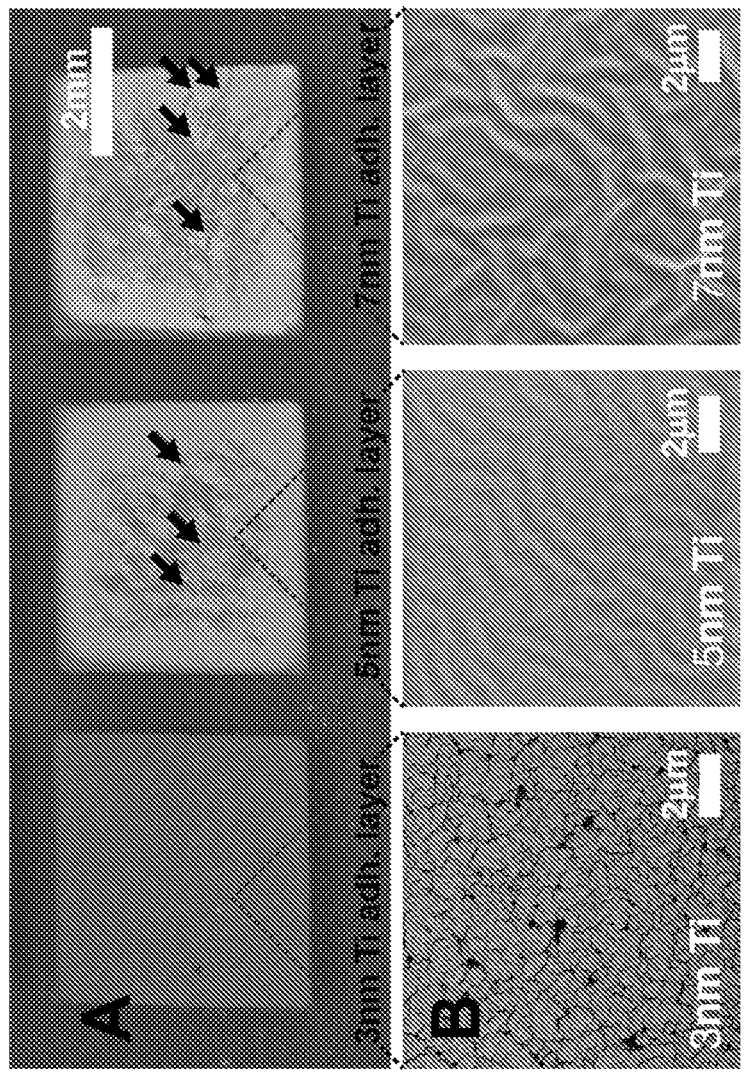
FIG. 9 includes photographic images (A) and scanning electron microscopy images (B) of 20 nm thick gold films over 3 nm, 5 nm, and 7 nm thick titanium adhesion layers deposited via E-beam deposition on 65 μm thick PDMS substrates illustrating the effect of titanium adhesion layer thickness on macroscopic and microscopic structure of the resulting gold films.

The inventors explored various thicknesses of titanium and gold layers for the Ti—Au—Ti piezoelectric sensors. Unexpectedly, the inventors realized that thicknesses of titanium and gold layers that produce functional and reliable piezoelectric wires on relatively thick PDMS layers (e.g., a 1 mm thick PDMS layer) did not produce functional and reliable piezoelectric wires on substantially thinner PDMS layers. The inventors discovered that the thickness of the applied titanium adhesion layer drives the morphology of the overlying gold film for relatively thin PDMS layers (e.g., about 100 nm thick or less). FIG. 9 includes images that illustrate the effect of titanium adhesion layer thickness on the macroscopic (A) and microscopic (B) structures of the resulting gold film layers when deposited on 65 µm PDMS layers. E-beam evaporation was used to deposit 4×4 mm squares of 3, 5, and 7 nm thick titanium adhesion layers followed by 20 nm thick gold layers on a 65 µm thick PDMS layer overlying a glass support. The upper photographic images (A) showed macroscopic crack development (indicated by the arrows) for the 5 nm and 7 nm titanium adhesion layers. Such macroscopic cracks often lead to defects in piezoelectric wires made from these materials. Notably these macroscopic crack defects are not observed for the thinner 3 nm titanium adhesion layers. The lower scanning electron microscopy (SEM) images (B) of the gold films show the micro-cracked structure in gold film on the 3 nm thick titanium adhesion layer. For gold films on 5 nm thick and thicker titanium adhesion layers, micro-wrinkled and continuous films are observed. It is possible that the microcracking of the gold layer on 3 nm titanium on the 65 µm thick PDMS layer, as opposed to microwrinkling of gold on 4 nm thick and 5 nm thick, relieves sufficient stress to prevent macroscopic crack defect formation. The microstructures appeared to be largely independent of the thickness of the gold films. On very thick PDMS layers (e.g., 1 mm thick) no macroscopic defects in gold layers were observed for 3 nm, 4 nm or 5 nm thick titanium adhesion layers; however, such PDMS layers are too thick to be employed in embodiments. As explained above, the strength of the strain signal is inversely proportional to the thickness of the first polymer substrate layer on which the wire is deposited. As such, it is desirable to deposit the wire on thinner PDMS layers to increase the strain signal.

Figure 10:
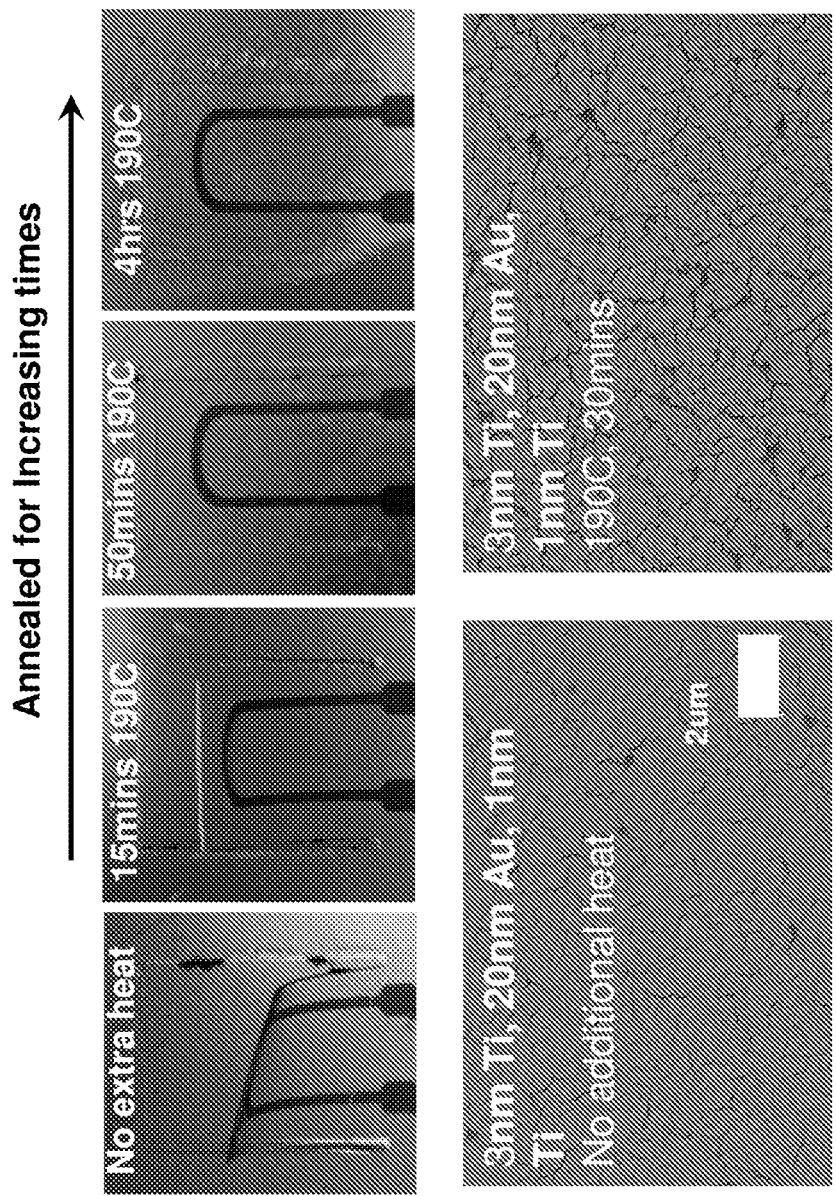
FIG. 10 includes images of cantilevers with Ti—Au—Ti wires exhibiting prestress and stress relaxation via annealing.

The process of depositing the wires creates prestress in the wires. To visualize this prestress during development of the process after deposition of the wires, the underlying PDMS layer was cut into a cantilever and was released from the rigid substrate. Bending of the cantilever evidenced the prestress in the wire. FIG. 10 includes images of the cantilever without annealing and after annealing for various amounts of time. The cantilevers shown in FIG. 10 included a 4 µm thick PDMS bottom layer (the first polymer substrate layer), with a 3 nm titanium adhesion layer, a 20 nm gold layer and a 1 nm titanium layer wire deposited on the PDMS bottom layer, and a 25 µm thick PDMS top layer (the second polymer substrate layer) deposited over the wire and the PDMS bottom layer. The image labeled "no extra heat" shows bending of the cantilever due to prestress. The image labeled "15 minutes" shows the reduced bending of the cantilever after annealing of the cantilever at 190 C for 15 minutes. The image labeled "50 minutes" shows that the cantilever no longer appears bent indicating full relaxation of the prestress after annealing of the cantilever at 190 C for 15 minutes. The image labeled "4 hours" shows that further annealing of the cantilever past 50 minutes to 4 hours did not seem to have any effect on the prestress as all prestress was relaxed after 50 minutes. The pre-stress in the cantilevers can be released by mild annealing at 190 C for 30-50 min. The scanning electron microscopy images of the wires showed that the annealing seemed to expand the micro-crack structure.

Resulting wires based on microcracked Ti—Au—Ti layers showed substantial elasticity. Bulk gold exhibits can be strained less than 1% prior to failure. However, the piezoelectric wires were cyclically strained 10% without failure. The resulting wires also exhibited a semi-linear strain relationship. The piezoelectric behavior of wires of 3 nm Ti, 20 nm gold and 1 nm titanium deposited on 4µ PDMS was tested using a machine, specifically a machine by INSTRON, that applies selected strains to materials. FIGS. 11A-11D show the resistance of the wires as a function of time when subjected to cycling straining of different magnitudes and different frequencies. In the low strain regime (e.g., below 1%) at relevant physiological frequencies (e.g., on the order of 1 Hz), the wires showed semi-linear strain-resistance relationship and that wire can (see FIG. 11A and FIG. 11B). The results also demonstrated that the wires could be repeatedly strained by at least 10% without failure (see FIG. 11C).

Measurements

Figure 12A:
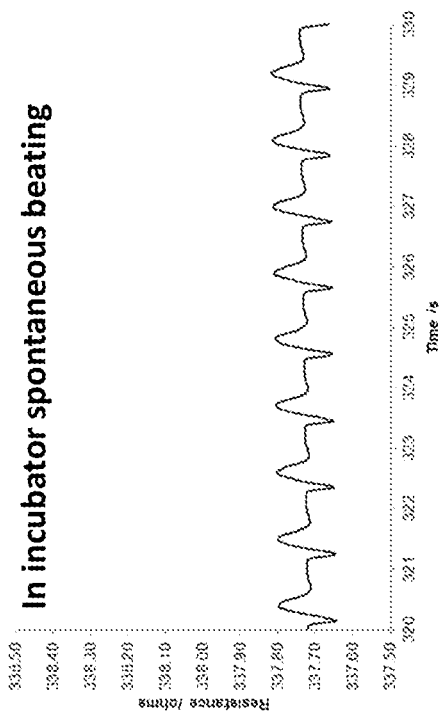
FIG. 12A is a graph of resistance versus time showing spontaneous contraction/beating of a muscle tissue layer on the device of Example 1.
Figure 12B:
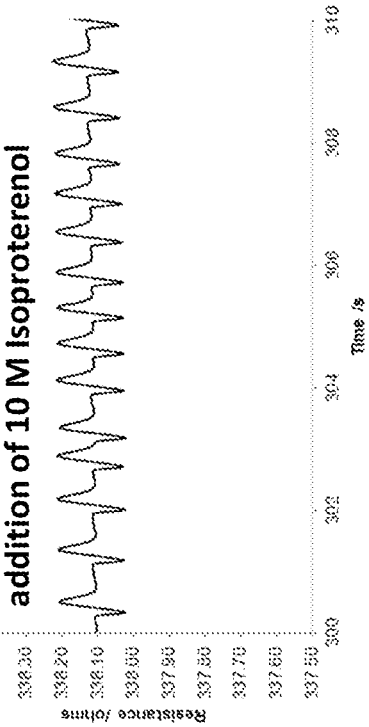
FIG. 12B is a graph of resistance versus time showing the effect of addition of 10 μM isoproterenol on the spontaneous beating of the muscle tissue layer on the device of Example 1.

As noted above, measurements were made of muscle tissue layers of NVRM muscle cells on the devices in the multiplexed apparatus. FIGS. 12A and 12B show measurements of resistance versus time evidencing spontaneous beating of the NVRM cells in the incubator. As shown in FIG. 12B, after addition of 10 µM isoproterenol, the spontaneous beating frequency of the cells significantly increased, providing proof of principle for use of the apparatus for measuring the effect of drugs on the function of muscle tissue layers.

Figures 13A, 13B:
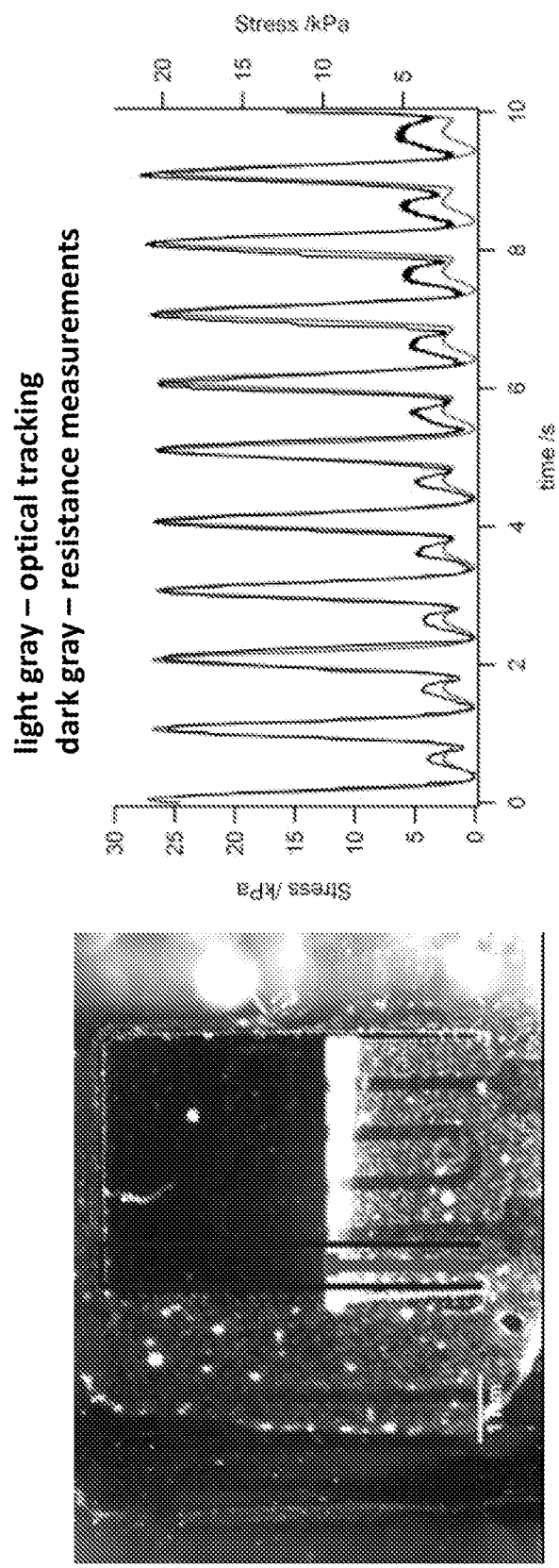
FIG. 13A is an image showing optical tracking of deflection of the cantilever in the device of Example 1.
FIG. 13B is a graph of stress versus time showing that both optical tracking of deflection of the cantilever (light gray) and electronic tracking of deflection based on resistance measurements (dark gray) showed similar results.

Tracking of cantilever deflection in devices via changes in resistance was compared to optical tracking of cantilever deflection. FIG. 13A is an image illustrating how optical tracking can be employed to measure cantilever deflection. An optical imaging device is set up with a planar view of cantilever device. As the device deflects in response to stress in the cantilever, the apparent cantilever length (i.e., the projection of the cantilever onto the plane of the substrate) shortens. Measuring the apparent length of the cantilever provides a measurement of the radius of curvature of the cantilever according to the following equations which are illustrated in part B of FIG. 8.

For $2L/\pi < R$ $x = R_0 \sin(L/R_0)$ and for $R \leq 2L/\pi$ $R_0 = x$ where $R_0$ is the radius of curvature, x is the projection onto the substrate and L is the cantilever length. The radius of curvature of the cantilever can be related to the stress in the muscle tissue layer through the equations in part (A) of FIG. 8. Other methods of planar optical measurement of cantilever deflection may be found in WO2010/0127280. FIG. 13B is a graph of stress versus time showing that both optical tracking of deflection of the cantilever (light gray) and tracking changes (dark gray) showed similar results.

Example 2—Fiber Guided Anisotropic Muscular Tissue Piezoresistive Strain Gauge Device with Micropatterned Chemical Cues and Multiplexed Apparatus A cantilever geometry device for measuring a contractile function of a muscle tissue layer that employed a pieozoresistive stretchable metal nanofilm wire embedded in a PDMS flexible substrate with fiber guided anisotropic tissue growth was produced. The tissue supporting layer employed a fiber construct to guide development of single layer to multilayer anisotropic muscle tissue. The device was similar to that of Example 1, except that instead of employing micropatterned chemical cues for anisotropic tissue growth, a fiber construct in the form of a sheet of fibers guided anisotropic tissue development. FIG. 14A schematically depicts the design of the device and FIG. 14B is an image of devices with the tissue supporting sheet of fibers attached.

Fabrication

Figure 15A:
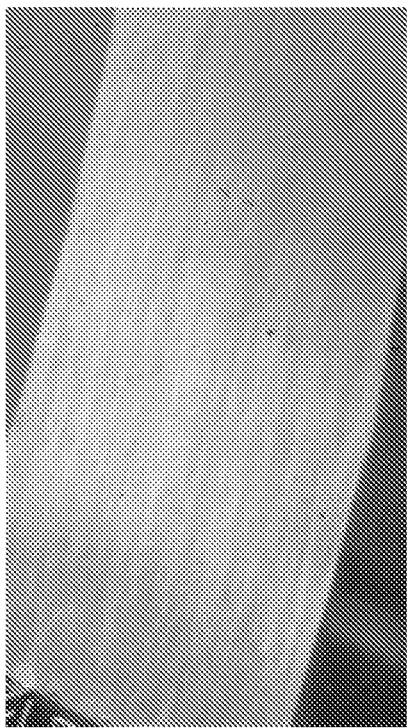
FIG. 15A is an image of a sheet of pull spun fibers used for the fiber construct.
Figure 15B:
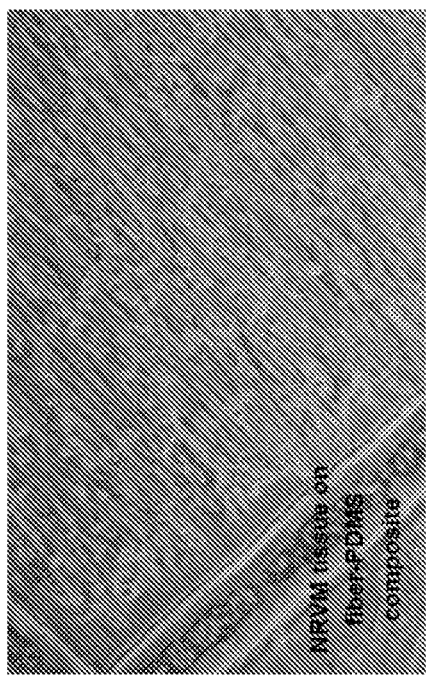
FIG. 15B is an image of NVRM anisotropic tissue that grew into the fiber sheet of a device.

Device fabrication similar to that described above for Example 1; however, after curing of the top PDMS layer (the second polymer substrate layer) at 65 C for one hour, a sheet of pull-spun polycaprolactone (PCL):gelatin fibers was transferred onto the flexible substrate and the PDMS was subsequently allowed to cure at room temperature. By controlling sheet thickness, thickness of tissue construct can be controlled. The ratio of PCL to gelatin was 4:1 by weight for the fibers. The individual fibers had a diameter of about 500 nm to 1 µm. However, in other embodiments the fibers could have a diameter in the range of 50 nm to 50 µm. Pull spinning was used for fabrication of fibrous scaffold as the technique was found to give optimal fiber alignment in combination with control of scaffold thickness as compared to rotary jet spinning. FIG. 15A is an image of the PCL:gelatin fiber sheet that is pull spun onto an ultra-high molecular weight polyethylene backing layer. The fiber sheets were about 25 µm thick. However, in other embodiments, fiber sheets could have a thickness anywhere in the range of 1 µm to 200 µm thick. NVRM cells were grown into anisotropic muscle tissue layers on the devices. FIG. 15B is an image of NVRM anisotropic tissue that grew into the fiber sheet of a device. Cardiomyocytes derived from human pluripotent stem cells were also grown into anisotropic muscle tissue layers on the devices. After the muscle tissue was grown the sacrificial release layer was removed to free the cantilever for each device.

Results

Figure 16A:
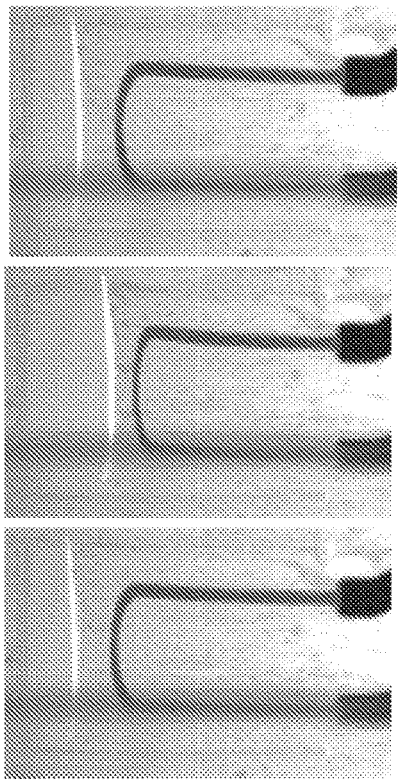
FIG. 16A includes images of devices according to the design of FIG. 14A showing deflection due to force from adhered muscle tissue.
Figure 16B:
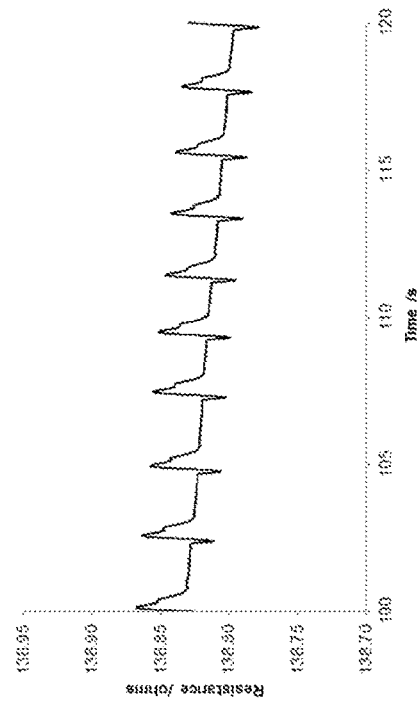
FIG. 16B is a graph of resistance versus time for a device according to the design of FIG. 14A with an NVRM muscle tissue layer showing spontaneous contraction of the tissue.

FIG. 16A includes images of the device showing deflection due to forces exerted by the ingrown muscle tissue layer. FIG. 16B is a graph of showing a record of the spontaneous contraction of NVRM tissue on the cantilever with the fiber sheet as a tissue supporting layer. The fibrous scaffolds supported development of thicker anisotropic muscular constructs than monolayers of cells. The applied constructs were furthermore found to support long term in vivo culture of NRVM based tissues over at least several weeks. Additionally, the scaffolds supported development of tissue based on cardiomyocytes derived from human induced pluripotent stem cells, which display no delamination, a problem frequently observed for muscular thin film tissue based e.g. on micro-contact printed fibronectin.

Example 3—Fully 3D Printed Groove-Guided Muscle Tissue Layer Strain Gauge Device A cantilever geometry device that can be fully 3D printed and employs tissue guiding micron scale grooves in a top surface of the flexible substrate is described. To determine the effectiveness of micro-grooves in the flexible substrate for formation and development of anisotropic muscle tissue, direct ink written microgrooved patterns of PDMS were formed on the top surface of a polymer substrate layer, and tissue development and growth was evaluated for the microgrooved patterns.

Fabrication

Figure 17:
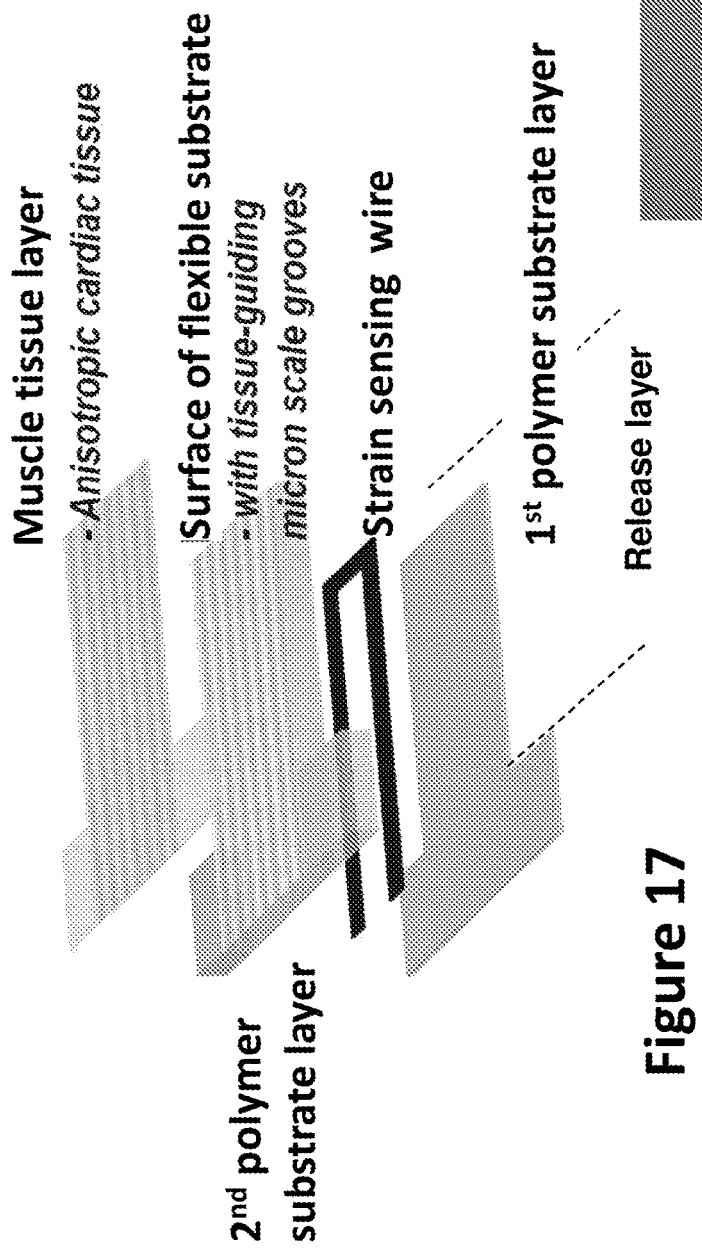
FIG. 17 schematically depicts an exploded view of layers of a fully direct ink written device having a flexible substrate with a microgrooved surface for directing anisotropic tissue growth.

Fabrication of the devices is by sequential direct ink writing of each layer using a 3D printer. FIG. 17 shows the different layers of a single device. Multiple devices can be produced using the 3D printer in the form of a multiplexed, multiwell apparatus. The inks used for writing the device should be selected for writing features at relevant length scales, as well as to give appropriate mechanical and electrical properties to the final device. A 2"×3" glass slide serves as substrate for the device using a custom print code. A release layer (e.g., 1 wt % dextran in 1:9 isopropanol:water) is written on the substrate. For biocompatible water soluble polymers used for sacrificial release layers, addition of a solvent such as isopropanol break solution surface tension in order to allow printing of the water soluble thin films. The first polymer substrate layer is written over the release layer and the substrate. The first polymer substrate layer may be any suitable polymer in any suitable solvent (e.g., PDMS (SYLGARD 184), which may be in a solvent). The patterned strain sensing wire is written over the first polymer substrate layer. The patterned strain sensing wire may be a conducting micro or nano particle doped polymer in a suitable solvent (e.g., 20 wt % carbon black particles in PDMS (DOW CORNING SE 1700) in decane). Conductive leads (e.g., conductive silver ink from Voxel8 Inc.) may also be written. For the printed leads, metal particle doped polymers are more conducting that their carbon black counterpart for similar loading volumes. For the part of the device that is not deformed by the cells, a mechanically robust and high conductivity printable composite is ideal. The second polymer substrate layer is written over the patterned strain sensing wire and the first polymer substrate layer. The second polymer layer may be any suitable polymer in any suitable solvent (e.g., PDMS (SYLGARD 184), which may be in a solvent). Cell aligning grooves are written on the second polymer layer using any suitable polymer (e.g., DOW Corning SE:1700 PDMS). Wells are also direct ink written over the devices using any suitable polymer (e.g., DOW Corning SE:1700 PDMS mixed 5:1 with SYLGARD 184 PDMS). The devices are incubated with fibronectin and subsequently seeded with NVRM cells. If the release layer is water soluble (e.g., dextran), the liquid medium used for NRVM cell seeding dissolves the sacrificial layers, releasing the cantilevers prior to growth and development of the muscle tissue layers.

For the cell aligning grooves: DOW Corning SE:1700 PDMS 1:25 curing agent:base gives a MPa range stiffness of the cured material. This highly viscous and shear-thinning PDMS enabled printing high aspect ratio tissue-aligning structures.

Figure 18:
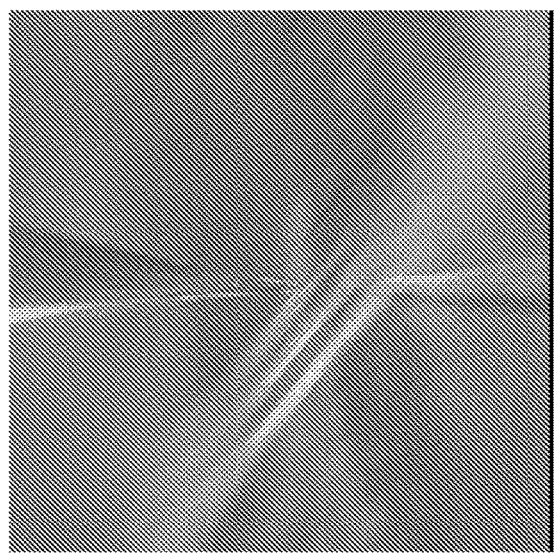
FIG. 18 is an image of a microgrooved surface being written on an underlying polymer substrate.

For purposes of evaluating the effect of microgroove properties on anisotropic tissue growth, PDMS lines were written onto an underlying polymer layer. Fabrication of the PDMS microgrooved surface was by direct ink writing of PDMS lines on the polymer layer using a 3D printer. The cell aligning grooves were written from DOW Corning SE:1700 PDMS mixed with 5:1 SYLGARD 184 PDMS with both mixtures having a ratio of 1:10 of curing agent: base. FIG. 18 shows the direct ink writing of the PDMS microgrooves using a 3D printer employing a 30 µm diameter writing tip. For the cell aligning grooves: DOW Corning SE:1700 PDMS 1:25 curing agent:base gives a MPa range stiffness of the cured material. This highly viscous and shear-thinning PDMS enabled printing high aspect ratio tissue-aligning structures. The microgrooved surfaces were incubated with fibronectin and then seeded with NRVM cells.

Results

Figure 19:
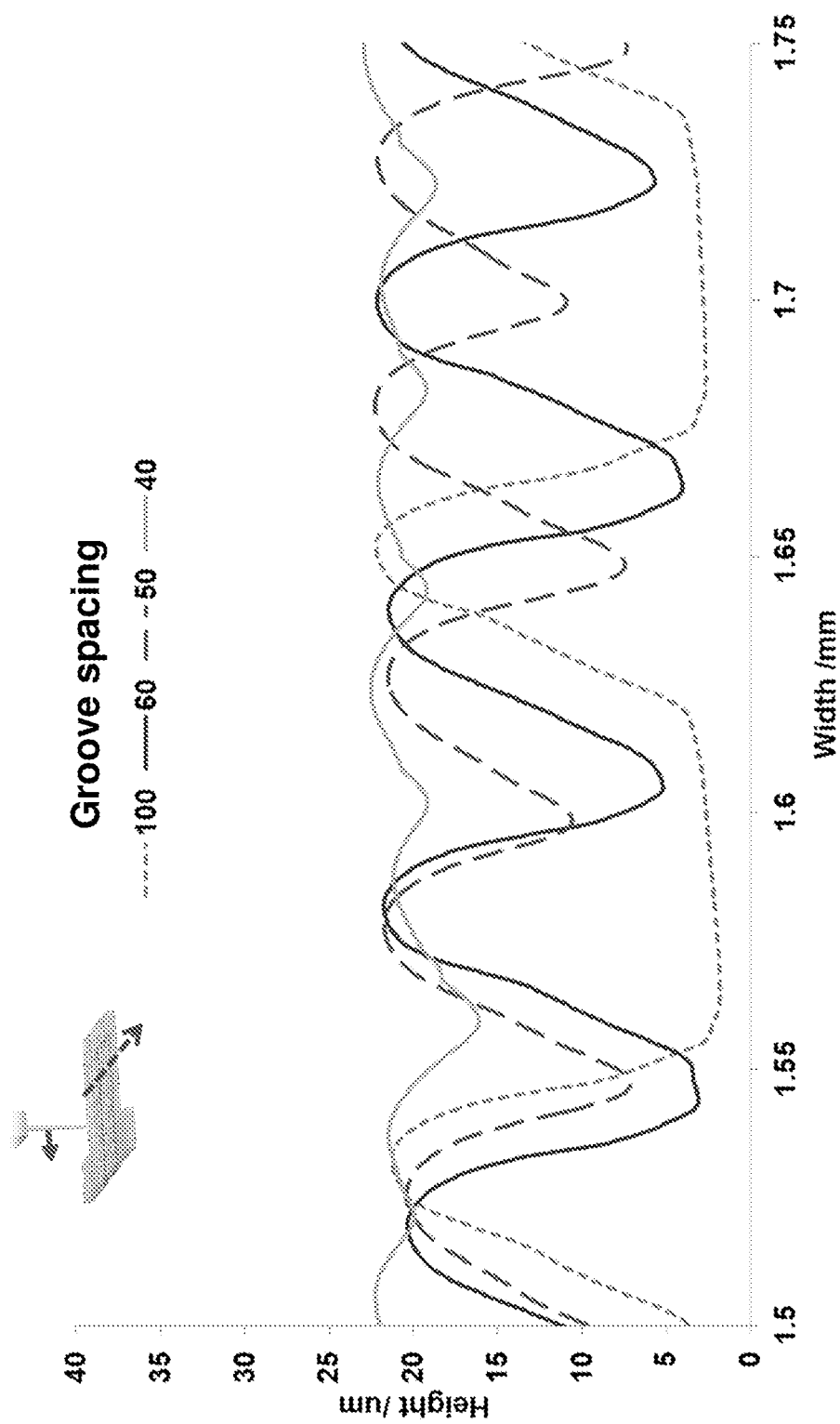
FIG. 19 includes height versus width profiles for microgrooved surfaces written with a 30 μm tip having different groove spacings.

FIG. 19 shows how the groove spacing affected the resulting profile of the top surface for PDMS lines written with a 30 µm diameter writing tip. A groove spacing of 40 µm produced only shallow grooves with a hill to valley height of less than 5 µm. A groove spacing of 100 µm produced hills separated by wide flat valleys. For the 30 µm diameter writing tip, a 50 µm to 60 µm groove spacing produced grooves with a hill to valley height of about 10 µm to 15 µm.

FIGS. 20A and 20B are confocal images of immunostained anisotropic NRVM tissue developed on microgrooved PDMS structures. As additional cells were added, the tissue layer thickened in the valleys of the grooves as shown in the side view of FIG. 20A. The quality of the anisotropic tissue layer grown on the devices was a function of groove spacing and groove structure. As shown in FIG. 20A, highly aligned tissue, as indicated by highly aligned sarcomeres, was achieved using a groove spacing of 50 µm. In contrast, the tissue on microgrooves with a spacing of 40 µm did not show alignment, likely due to this spacing creating only shallow grooves (e.g., less than 5 µm) for lines written with a 30 µm diameter writing tip (see FIG. 20B). The tissues on microgrooves with a spacing of 100 µm was low quality as the gap was too wide to be spanned by the tissues (see FIG. 20B). For the 30 µm writing tip, a 50 µm to 60 µm groove spacing seemed to produce the best results for anisotropic tissue layer development.

Figures 21A, 21B:
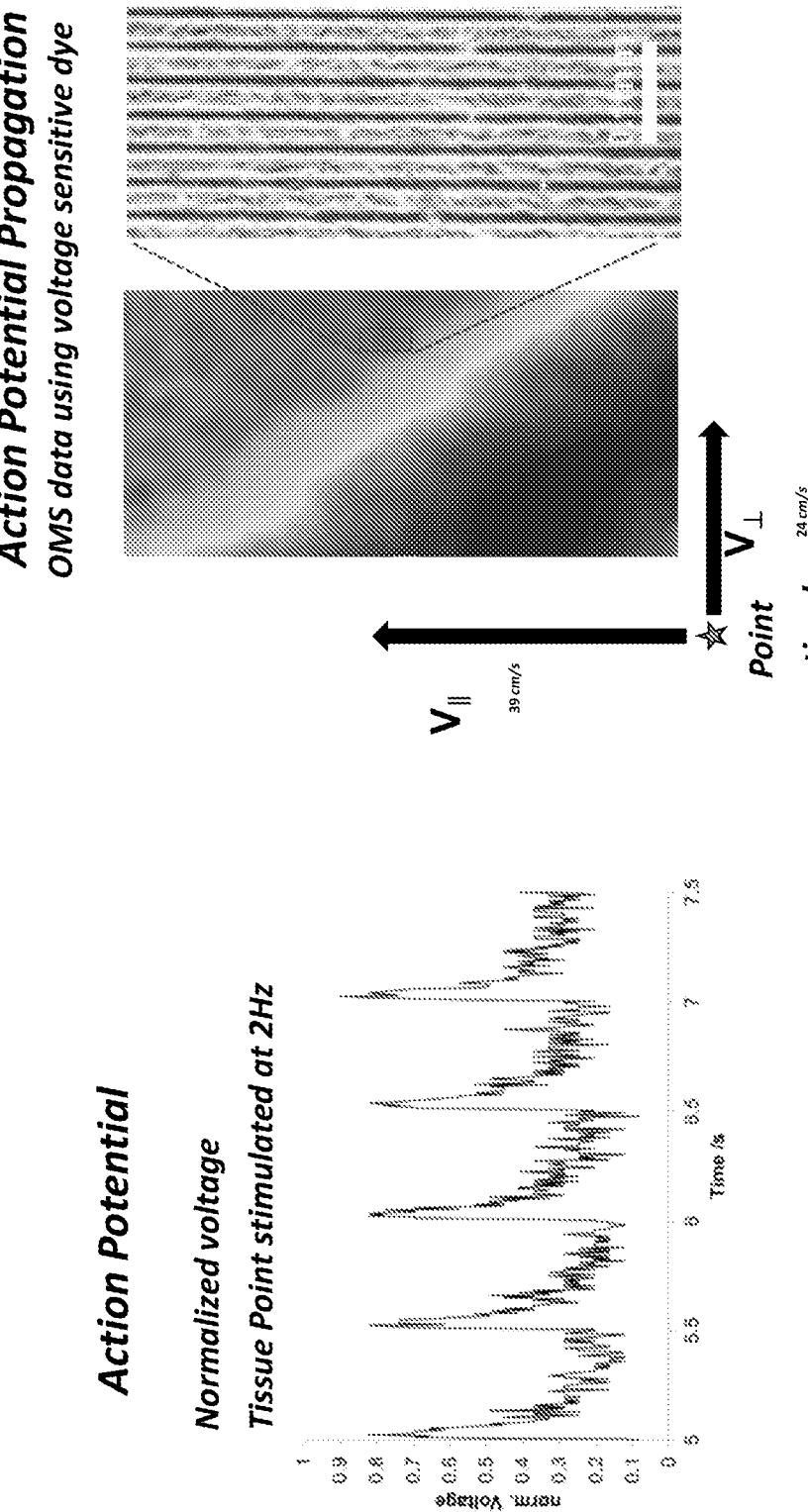
FIG. 21A is a graph of an action potential from 2 Hz tissue point stimulation of an anisotropic tissue layer on a microgrooved surface.
FIG. 21B shows optical mapping of action potentials in the anisotropic tissue layer using a voltage sensitive dye to show anisotropic conduction of the action potential.

As shown in FIGS. 21A and 21B, application of voltage sensitive dye and optical mapping confirmed the electrical anisotropy of tissue guided by the direct ink written microgrooves, as indicated by anisotropic conduction velocity of action potential.

Example 4—Planar Sensor Fabrication

Due to the 1-100 kPa required effective stiffness of the flexible substrate in the deformation zone (e.g., within 50 µm of the tissue layer) in the planar geometry, only a subset of the suggested wire materials are applicable in this layout.

Wire materials based on percolating networks of particles, either in the form of composites or as discontinuous sheets, as well as conductive inks/liquids, are of thus of special relevance for the planar configuration.

In the case of particle-based conductors, one fabrication route includes a suspension of conducting particles, such as carbon nanotubes (CNT), carbon black (CB), gold nanoparticles or similar, is locally ink-jet printed or direct-ink written 3D printed onto a 4 mm thick PDMS substrate, which has low crosslinking density and a resultant Young's modulus below 100 kPa. by adjusting the concentration of particles in the printing solvent, the thickness of the printed wire can be kept below 100 nm. A coating of the compliant PDMS of a thickness of <2 µm is the added on top of the substrate, through spin-coating or spray-coating, diluting non-cured PDMS into hexane, octane, decane, or similar.

Finally, micropatterned guiding fibronectin lines are transferred to the substrate using micro-contact printing or inkjet printing. In order not to constrain the tissue contraction, the substrate should be free to move, and thus not clamped in at the edges near the tissue. Consequently highly compliant liquid wells should be applied to contain the cell medium, or the applied wells should have a radius large enough to not significantly constrain the deformation of the support and wires below the localized muscle tissue.

In an alternative case, conducting liquids can be applied. These can be embedded into a compliant substrate (e.g. through capillary filling of micro-fluidic channels or through direct-ink writing into a compliant substrate such as non-cured PDMS which is cured subsequently to printing).

U.S. Provisional Patent Application No. 61/905,489, filed Nov. 18, 2013 and entitled "Printable Stretchable Strain Sensor", the contents of which are incorporated herein in their entirety, describes strain sensors and methods of making highly deformable soft strain sensors that include an elastomeric body with a strain sensitive structure embedded therein. Such methods of making strain sensor could be modified by selecting appropriate thicknesses and employing structural and chemical cues to form the flexible substrates to which the MTFs are adhered. Such flexible substrates could be employed for either or both of the out of plane bending (A) and the in plane strain (B) approaches.

As will be recognized by those of ordinary skill in the pertinent art based on the teachings herein, numerous changes and modifications may be made to the above-described and other embodiments and examples of the present disclosure without departing from the spirit of the invention as defined in the appended claims. Accordingly, this detailed description of embodiments is to be taken in an illustrative, as opposed to a limiting, sense. Those skilled in the art will recognize, or be able to ascertain using no more than routine experimentation, many equivalents to the specific embodiments of the described herein. Such equivalents are intended to be encompassed by the following claims. Further, one of ordinary skill in the art will appreciate that aspects of the embodiments and examples described herein can be combined in various ways that fall within the scope of the invention.

The invention claimed is:

1. A method of measuring a contraction of a muscle tissue, the method comprising:
   providing a muscle tissue layer adhered to an underlying flexible substrate comprising one or more strain-sensitive electrical elements configured to have a change in resistance in response to strain in the flexible substrate;
   providing a stimulus to the muscle tissue layer under conditions such that the muscle tissue layer contracts causing strain in the flexible substrate and in the one or more strain-sensitive electrical elements; and
   measuring a change in resistance of the one or more strain-sensitive electrical elements and relating the measured change in resistance to a force exerted on the flexible substrate by contraction of the muscle tissue layer.

2. The method of claim 1, wherein the flexible substrate further comprises a hydrogel layer at least partially overlying the one or more strain-sensitive electrical elements.

3. The method of claim 1, wherein the contraction of the muscle tissue layer causes the strain in the flexible substrate and out of plane bending of the flexible substrate.

4. The method of claim 1, further comprising:
contacting the muscle tissue layer with a candidate compound; and
measuring a second change in resistance of the one or more strain-sensitive electrical elements in the presence of the candidate compound when a contraction stimulus is applied, wherein a difference between the change in resistance in the absence of the candidate compound and the second change in resistance in the presence of the candidate compound indicates the candidate compound modulates contraction of the muscle tissue layer.

5. The method of claim 1, wherein the strain in the flexible substrate is in-plane strain of the flexible substrate due to contractions of the muscle tissue layer without out of plane deflection of the flexible substrate.

6. The method of claim 1, wherein one or more strain-sensitive electrical elements comprise wires embedded in the flexible substrate.

7. The method of claim 1, wherein one or more strain sensitive electrical elements comprise particles embedded in the flexible substrate.

8. A method of measuring a contraction of a muscle tissue, the method comprising:
providing an actively contractile muscle tissue layer adhered to an underlying flexible substrate comprising one or more strain-sensitive electrical elements configured to have a change in resistance in response to strain in the flexible substrate, wherein the actively contractile muscle tissue layer causes strain in the flexible substrate layer and in the one or more strain-sensitive electrical elements; and
measuring a change in resistance of the one or more strain-sensitive electrical elements and relating the measured change in resistance to a force exerted on the flexible substrate by contraction of the actively contractile muscle tissue layer.

9. The method of claim 8, wherein the flexible substrate further comprises a hydrogel layer at least partially overlying the one or more strain-sensitive electrical elements.

10. The method of claim 8, wherein the contraction of the actively contractile muscle tissue layer causes the strain in the flexible substrate and out of plane bending of the flexible substrate.

11. The method of claim 8, wherein the strain in the flexible substrate is in-plane strain of the flexible substrate layer due to contractions of the actively contractile muscle tissue layer without out of plane deflection of the flexible substrate.

12. The method of claim 8, further comprising:
contacting the muscle tissue layer with a candidate compound; and
measuring a second change in resistance of the one or more of strain-sensitive electrical elements in the presence of the candidate compound when a contraction stimulus is applied, a difference between the change in resistance in the absence of the candidate compound and the second change in resistance in the presence of the candidate compound indicates the candidate compound modulates contraction of the muscle tissue layer.

13. The method of claim 8, wherein the one or more strain-sensitive electrical elements comprise wires embedded in the flexible substrate.

14. The method of claim 8, wherein the one or more strain sensitive electrical elements comprise particles embedded in the flexible substrate.

* * * * *